United States Patent
Arai et al.

(10) Patent No.: US 10,317,397 B2
(45) Date of Patent: Jun. 11, 2019

(54) MICROPARTICLE SEPARATION CHIP, AND MICROPARTICLE SEPARATION SYSTEM AND MICROPARTICLE SEPARATION METHOD WHICH EMPLOY SAID MICROPARTICLE SEPARATION CHIP

(71) Applicant: National University Corporation Nagoya University, Nagoya-shi, Aichi (JP)

(72) Inventors: Fumihito Arai, Aichi (JP); Taisuke Masuda, Aichi (JP); Woneui Song, Aichi (JP)

(73) Assignee: NATIONAL UNIVERSITY CORPORATION NAGOYA UNIVERSITY, Nagoya-Shi, Aichi (JP)

( * ) Notice: Subject to any disclaimer, the term of this patent is extended or adjusted under 35 U.S.C. 154(b) by 192 days.

(21) Appl. No.: 15/303,040

(22) PCT Filed: Apr. 9, 2015

(86) PCT No.: PCT/JP2015/061059
§ 371 (c)(1),
(2) Date: Oct. 10, 2016

(87) PCT Pub. No.: WO2015/156343
PCT Pub. Date: Oct. 15, 2015

(65) Prior Publication Data
US 2017/0122937 A1    May 4, 2017

(30) Foreign Application Priority Data

Apr. 11, 2014  (JP) .................................. 2014-081700

(51) Int. Cl.
*G01N 33/543*    (2006.01)
*G01N 33/574*    (2006.01)
(Continued)

(52) U.S. Cl.
CPC .. *G01N 33/54313* (2013.01); *B01L 3/502761* (2013.01); *G01N 33/54306* (2013.01);
(Continued)

(58) Field of Classification Search
CPC ........... G01N 33/54313; G01N 33/543; G01N 33/547; G01N 33/53; G01N 33/50; G01N 33/48; G01N 33/545
(Continued)

(56) References Cited

U.S. PATENT DOCUMENTS 5,427,663 A    6/1995  Austin et al.
6,027,623 A *  2/2000  Ohkawa ........... G01N 27/44704
                                                  204/450
(Continued)

FOREIGN PATENT DOCUMENTS

JP    H09-504362 A    4/1997
JP    2001-296219 A   10/2001
(Continued)

OTHER PUBLICATIONS

Feng et al, Accurate dispending system for single oocytes using air ejection, Biomicrofluidics, 7, 2013, 054113. (Year: 2013).*
(Continued)

*Primary Examiner* — Christine T Mui
(74) *Attorney, Agent, or Firm* — McDermott Will & Emery LLP

(57) ABSTRACT

Provided is a microparticle separation system capable of continuously separating microparticles from a solution in a short period of time in which microparticles having different particle diameters are mixed, without the need to use antibodies or the like. The microparticle separation system comprises a microparticle separation chip; a thin plate for a sample liquid; a thin plate for a sheath liquid; and suctioning means and/or a suctioning device for suctioning the sheath
(Continued)

liquid; and the microparticle separation chip comprises a single capture site for capturing to-be-captured microparticles being formed using the at least three pillars having one end provided on the substrate and the other end open upward.

21 Claims, 13 Drawing Sheets

(51) Int. Cl.
  *B01L 3/00* (2006.01)
  *G01N 33/50* (2006.01)

(52) U.S. Cl.
  CPC ..... *G01N 33/54366* (2013.01); *G01N 33/574* (2013.01); *B01L 2200/0668* (2013.01); *B01L 2300/04* (2013.01); *B01L 2400/0487* (2013.01); *B01L 2400/086* (2013.01)

(58) Field of Classification Search
  USPC ........... 422/502, 500, 50; 435/6, 325, 283.1, 435/252.1; 436/6, 325, 283.1, 252.1
  See application file for complete search history.

(56) References Cited

U.S. PATENT DOCUMENTS

| | | | | |
|---|---|---|---|---|
| 6,451,264 | B1 * | 9/2002 | Bhullar | B01L 3/502746 204/451 |
| 8,304,230 | B2 * | 11/2012 | Toner | B01L 3/502746 435/288.5 |
| 2003/0049563 | A1 | 3/2003 | Iida et al. | |
| 2003/0119034 | A1 | 6/2003 | Kang et al. | |
| 2009/0098541 | A1 | 4/2009 | Southern et al. | |
| 2011/0003303 | A1 | 1/2011 | Pagano et al. | |
| 2012/0028349 | A1 | 2/2012 | Giorgini et al. | |
| 2015/0246353 | A1 * | 9/2015 | Arai | B01L 3/502753 435/2 |

FOREIGN PATENT DOCUMENTS

| | | | | |
|---|---|---|---|---|
| JP | 2003-315349 | A | 11/2003 | |
| JP | 2004-045357 | A | 2/2004 | |
| JP | 2008-539711 | A | 11/2008 | |
| JP | 2011-163830 | A | 8/2011 | |
| JP | 2012-530246 | A | 11/2012 | |
| JP | 6326582 | | * 4/2018 | ............. G01N 1/04 |
| WO | WO 94/29707 | | * 12/1994 | ............. G01N 27/26 |

OTHER PUBLICATIONS

Extended European Search Report issued in corresponding EP Patent Application No. 15776138.8, dated Nov. 23, 2017.
Allard, W. Jeffrey, et al. "Tumor cells circulate in the peripheral blood of all major carcinomas but not in healthy subjects or patients with nonmalignant diseases." Clinical Cancer Research 10.20 (2004): 6897-6904.
Riethdorf, Sabine, et al. "Detection of circulating tumor cells in peripheral blood of patients with metastatic breast cancer: a validation study of the CellSearch system." Clinical Cancer Research 13.3 (2007): 920-928.
Tan, Swee Jin, et al. "Microdevice for the isolation and enumeration of cancer cells from blood." Biomedical microdevices 11.4 (2009): 883-892.
Mohamed, Hisham, et al. "Isolation of tumor cells using size and deformation." Journal of Chromatography A 1216.47 (2009): 8289-8295.
International Preliminary Report on Patentability issued in corresponding International Patent Application No. PCT/JP2015/061059, dated Apr. 21, 2016.
Search Report issued in corresponding International Application No. PCT/JP2015/061059, dated Jun. 16, 2015.

* cited by examiner cover glass

MICROPARTICLE SEPARATION CHIP, AND MICROPARTICLE SEPARATION SYSTEM AND MICROPARTICLE SEPARATION METHOD WHICH EMPLOY SAID MICROPARTICLE SEPARATION CHIP

CROSS REFERENCE

This application is the U.S. National Phase under 35 U.S.C. § 371 of International Application No. PCT/JP2015/061059, filed on Apr. 9, 2015, which claims the benefit of Japanese Application No. 2014-081700, filed on Apr. 11, 2014, the entire contents of each are hereby incorporated by reference.

TECHNICAL FIELD

The present invention relates to a microparticle separation chip (may hereinafter be referred to merely as "chip") for separating microparticles of different sizes mixed in a liquid, and to a microparticle separation system and method using the chip; and more particularly relates to a chip for separating circulating tumor cells ("CTCs"), and a CTC separation system and method for CTC separation using the chip, for selectively capturing CTCs in blood.

CTCs are defined as tumor cells that circulate through the peripheral bloodstream of a patient, and have infiltrated the blood vessels from a primary tumor or a metastatic tumor. Detection of CTCs has received attention in recent years as a method of early detection of metastatic malignant tumors because this method is less invasive than radiography and detection of tumor markers in blood serum, allows accurate diagnosis of metastatic malignant tumors, and may be used as an indicator of patient prognosis prediction and treatment effect.

CTCs are very rare cells and it is known that only about one cell is present in $10^8$ to $10^9$ blood cells contained in the blood of a metastatic cancer patient. For this reason, considerable effort is being given to technical development for accurately detecting rare CTCs from peripheral blood. Principal detection methods developed heretofore include immunohistochemical analysis, PCR analysis, and flow cytometry. However, since CTCs are very rare cells as mentioned above, it is not possible to provide a method for detecting such cells directly from blood. Therefore, a CTC concentration procedure is therefore ordinarily essential as a pretreatment, and the CTC abundance ratio must be brought to a level that falls within the range of the detection method.

Among the various techniques developed as CTC concentration methods, the most widely used methods involve concentration of tumor cells in which specific antigens on the surface of the cells have been targeted. Most of the methods use a technique in which magnetic microparticles, which have immobilized monoclonal antibodies against epithelial cell adhesion molecules (EpCAM), are mixed with blood, and tumor cells are thereafter concentrated using a magnet (see, e.g., Non-Patent Document 1). However, it is known that the expression level of EpCAM varies considerably depending on the type of tumor.

Other concentration methods include techniques for concentration using the size of the cell or other modes as a reference. Isolation by size of epithelial tumor cells (ISET) is a method for filtering and sorting epithelial tumor cells that are larger in size than white blood cells. ISET is a simple method in that blood is filtered using a polycarbonate membrane filter having a pore size of 8 μm, and the method is inexpensive and user friendly. The polycarbonate membrane filter used in this case has pores that are formed by heavy ion irradiation and etching by track etching. However, there is a problem in that the pores have a relatively low density, and two or more pores sometimes overlap. Therefore, the capture efficiency for CTC capture is 50 to 60%, and a simple yet efficient concentration method has yet to be developed.

In order to make CTC detection efficient and accurate, techniques for concentration and detection must be carried out in a consistent manner. Multistage handling operations, e.g., cell dyeing, washing, separation, dispensing, and other operations create CTC loss, and it is preferred that these operations be avoided to the extent possible and that analysis be performed in a single process in an integrated detection device. Cellsearch (Veridex™, Warren, Pa.) is the only device that has received FDA approval as a CTC detection device. This device concentrates CTCs using magnetic microparticles with immobilized anti-EpCAM antibodies in whole blood, the tumor cells are immunostained, and the tumor cells are thereafter counted using an automated fluorescence microscope (see, e.g., Non-Patent Document 2). However, when the device is to be used, large-scale equipment is generally required, a trained operator must be available, and it is difficult to perform accurate bedside examinations in a short period of time.

On the other hand, a small microfluidic device for CTC detection is also known. For example, the microfluidic device for CTC detection developed by Toner, et al. is referred to as a CTC-chip and is composed of 78,000 cylindrical structures (micro-posts) in a silicon channel formed by photolithography. Anti-EpCam antibodies are coated on the micro-posts, and when blood is sent to the main channel, CTCs in the blood are captured on the micro-posts. The captured CTCs are subjected to immunofluorescence staining which targets an epithelial cell marker (cytokeratin), and the tumor cells are counted using a fluorescence microscope. This device is a small device that fits in the palm of the hand, and yet has a significant advantage in being capable of providing direct analysis of 5 mL or more of blood. It actually detects CTCs from the blood of a metastatic cancer patient, and is capable of detecting mutations that produce resistant to tyrosine kinase inhibitors from recovered CTCs. Although CTC detection using Cellsearch or a CTC-chip has undergone thoroughgoing experimentation and produced results using metastatic cancer patient blood and other actual samples, these techniques operate on the principle of concentrating CTCs using anti-EpCAM antibodies. There is therefore a problem in that EpCAM-negative or slightly positive tumor cells cannot be detected.

In another method, microfluidic devices for detecting CTCs are being developed using the size and mode of tumor cells as an indicator. In these devices, a membrane micro filter, a crescent-shaped cell-capturing well (see Non-Patent Document 3), or channels having four magnitudes of narrowness (see Non-Patent Document 4) are arranged in the channel structures thereof, and blood cells and tumor cells in the blood are sorted by size to selectively concentrate the tumor cells. The concentrated cells can be dissolved or otherwise manipulated in continuous fashion using the channels. A CTC recovery efficiency of 80% or more is obtained in experiments for evaluating the recovery efficiency of model tumor cells using these devices. However, the evaluation was performed by experimentation using model cells, and no study has been performed in relation to underlying technologies such as cell dyeing and/or washing operations that would be required during actual CTC detection. Furthermore, no experiments have been performed using cancer patient blood or other actual samples, and it is not apparent that these devices could be actually be used for CTC detection.

Furthermore, known small devices that do not use anti-EpCAM antibodies include microfluidic devices provided with a micro-cavity array (very small through-holes) in the microchannels to allow CTCs to be captured (see Patent Document 1). However, the microfluidic devices are of a type that capture CTCs in very small through-holes and therefore have a problem in that work efficiency is reduced due to CTC clogging, and it is furthermore difficult to recover the separated CTC.

In order to solve the above-described problems, the present inventors made a patent application (see Patent Document 2) having found that microparticles can be caused to precipitate using a force generated by a meniscus at the air-liquid boundary and capture only objective microparticles in capture sites using (1) a microchannel microparticle separation chip in which are formed main channels and a capture site, which has a greater width than that of the main channels, or (2) a microchannel microparticle separation chip in which are formed main channels, branching channels that branch from the main channels and reconnect to the main channels, and a capture site, which has a greater width than that of the branching channels, provided to the branching channels.

The present inventors made a patent application (see Patent Document 3) with a further novel finding in which objective microparticles can be captured and separated out with good efficiency by (1) mounting a microchannel microparticle separation chip, in which the main channels including capture sites are formed in radial fashion from the center of a substrate, on rotation means, (2) arranging an advection-aggregation unit comprising at least a sheath injection port, a sample injection port, a planar section for sheath liquid advection and aggregation, and a planar section for sample advection and aggregation, on the surface of the microchannel microparticle separation chip, (3) and injecting the sheath liquid and the sample liquid while the rotation means is rotated, whereby the sample can be continuously fed to the microchannel microparticle separation chip.

However, the microchannel microparticle separation chip described in Patent Documents 2 and 3 has a structure for capturing microparticles using very small microchannels and capture sites formed in the microchannels. Consequently, there is a problem in that the volume per unit time of a liquid capable of flowing through the microchannels is limited, and time is still required for the microparticle separation operation.

RELATED ARTS LIST

Patent Documents

Patent Document 1: Japanese Laid-open Patent Publication No. 2011-163830
Patent Document 2: Japanese Patent Application No. 2012-227717
Patent Document 3: Japanese Patent Application No. 2013-106824

Non-Patent Documents

Non Patent Document 1: Allard W J, Matera J, Miller M C, Repollet M, Connelly M C, Rao C, Tibbe A G, Uhr J W, Terstappen L W. 2004. Tumor cells circulate in the peripheral blood of all major carcinomas but not in healthy subjects or patients with nonmalignant diseases. Clin Cancer Res 10(20):6897-904.
Non Patent Document 2: Riethdorf S, Fritsche H, Muller V, Rau T, Schindlbeck C, Rack B, Janni W, Coith C, Beck K, Janicke F and others. 2007. Detection of circulating tumor cells in peripheral blood of patients with metastatic breast cancer: a validation study of the CellSearch system. Clin Cancer Res 13(3):920-8.
Non Patent Document 3: Tan S J, Yobas L, Lee G Y, Ong C N, Lim C T. 2009. Microdevice for the isolation and enumeration of cancer cells from blood. Biomed Microdevices 11(4):883-92.
Non Patent Document 4: Mohamed H, Murray M, Turner J N, Caggana M. 2009. Isolation of tumor cells using size and deformation. J Chromatogr A 1216(47):8289-95.

SUMMARY OF THE INVENTION

Problems to be Solved by the Invention

The present invention was devised in order to solve the above-described problems in the related art, and after having performed thoroughgoing research, the inventors perfected the invention upon making the novel finding that by forming a chip in which:

(1) a capture location is formed by pillars provided on the substrate, (2) the spacing of the pillars is set so that the microparticles to be removed may pass, but the microparticles to be captured cannot pass, and (3) at least three or more pillars for forming a single capture location are arranged in a positional relationship in which captured to-be-captured microparticles cannot flow out from between any adjacent pillars, a sample can flow to the entire substrate and throughput can be improved.

An object of the present invention is to provide a microparticle separation chip, and microparticle separation system and method using the microparticle separation chip.

Means to Solve the Problems

As described below, the present invention relates to a microparticle separation chip, and microparticle separation system and method using the microparticle separation chip.
(1) A microparticle separation chip, comprising a substrate and at least three or more pillars,
a single capture site for capturing to-be-captured microparticles being formed using the at least three or more pillars having one end provided on the substrate and the other end open above,
the spacing Z between any mutually adjacent pillars that form the single capture site being $Y<Z \leq X$, where X is the size of the to-be-captured microparticles, and Y is the size of the microparticles to be removed, and
the at least three or more pillars that form a single capture site being arranged in a positional relationship in which to-be-captured microparticles captured in the capture site do not flow out from between any adjacent pillars.
(2) The microparticle separation chip according to (1) above, wherein the spacing Z between the any mutually adjacent pillars is one selected from $0.8Y<Z \leq X0.8X$, $Y<Z \leq 0.8X$, and $0.8Y<Z \leq X$.
(3) The microparticle separation chip according to (1) or (2) above, wherein a plurality of capture sites is formed.

(4) The microparticle separation chip according to (3) above, wherein the plurality of formed capture sites are disposed adjacent to each other, and adjacent capture sites share a pillar.

(5) The microparticle separation chip according to (4) above, wherein the capture sites are disposed in a polygonal plane-filling state.

(6) The microparticle separation chip according to (5) above, wherein the polygon is one selected from an equilateral triangle, a square, and an equilateral hexagon.

(7) The microparticle separation chip according to any of (1) to (6) above, wherein the to-be-captured microparticles are CTCs and the microparticles to be removed are blood cells.

(8) The microparticle separation chip according to any of (1) to (7) above, wherein the substrate is polygonal or circular and a stepped part is formed at the external periphery of the substrate.

(9) The microparticle separation chip according to any of (1) to (7) above, wherein the substrate is polygonal and a planar section in which a pillar is not formed is formed at the external periphery of the substrate.

(10) The microparticle separation chip according to any of (1) to (7) above, wherein the substrate is circular and a planar section in which a pillar is not formed is formed at the external periphery of the substrate.

(11) A microparticle separation system comprising: the microparticle separation chip according to any of (1) to (10) above; a thin plate for sample liquid; a thin plate for sheath liquid; and suction means and/or a suction device for suctioning sheath liquid.

(12) A microparticle separation system comprising: the microparticle separation chip according to any of (1) to (10) above; a cover plate; and suction means and/or a suction device.

(13) The microparticle separation system according to (11) or (12) above, furthermore comprising a suction unit having a lateral groove and a suction hole in communication with the lateral groove.

(14) A suction unit comprising lateral groove and a suction hole in communication with the lateral groove, wherein one side surface of two side surfaces sandwiching the lateral groove is formed to be shorter than the two end sections of the suction unit and the other side surface.

(15) The suction unit according to (14) above, wherein the lateral groove has a width that allows liquid to be suctioned by capillary force.

(16) The suction unit according to (14) above, wherein the lateral groove has a width that allows insertion of suction means.

(17) A microparticle separation chip comprising at least:
the microparticle separation chip according to (10) above;
an advection-aggregation unit having at least a sheath liquid injection port, a sample injection port, a planar section for sheath liquid advection and aggregation, and a planar section for sample advection and aggregation;
rotation means for rotating the microparticle separation chip; and
suction means and/or a suction device for suctioning the sheath liquid.

(18) The microparticle separation system according to (17) above, wherein the advection-aggregation unit furthermore comprises a sheath liquid suction port and a hole for mounting a sheath liquid suction pad.

(19) The microparticle separation system according to (17) or (18) above, wherein the advection-aggregation unit furthermore comprises a sheath liquid suction port and a hole for suctioning sheath liquid by capillary force.

(20) A microparticle separation method comprising: injecting a sample liquid between a thin plate for a sample liquid and the microparticle separation chip according to any of (1) to (10) above; injecting a sheath liquid between a thin plate for a sheath liquid and the microparticle separation chip; and causing the microparticle separation chip, the thin plate for a sample liquid and the thin plate for a sheath liquid to move in a relative fashion to generate a meniscus, whereby to-be-captured microparticles are captured in capture sites provided to the microparticle separation chip, and microparticles to be removed are removed from the microparticle separation chip by the sheath liquid suctioned by suction means and/or a suction device.

(21) A microparticle separation method comprising: injecting a sample liquid between a cover plate and the microparticle separation chip according to any of (1) to (10) above; and capturing to-be-captured microparticles in capture sites provided to the microparticle separation chip by a meniscus generated as a result of the sample liquid being suctioned by suction means and/or a suction device.

(22) The microparticle separation method according to (21) above, comprising: injecting a sheath liquid between the cover plate and the microparticle separation chip after the sample liquid has been suctioned; and suctioning the sheath liquid with the aid of suction means and/or a suction device to thereby wash away remaining microparticles to be removed.

(23) A microparticle separation method comprising:
mounting the microparticle separation chip according to (10) above on rotation means for rotating the microparticle separation chip;
arranging an advection-aggregation unit having at least a sheath liquid injection port, a sample injection port, a planar section for sheath liquid advection and aggregation, and a planar section for sample advection and aggregation, on the surface of the microparticle separation chip;
injecting the sheath liquid from the sheath liquid injection port and injecting the sample liquid from the sample injection port while the rotation means is rotated to thereby move the microparticle separation chip and the planar section for sheath liquid advection and aggregation and the planar section for sample advection and aggregation in a relative fashion, and capture objective microparticles in the capture sites formed in the microparticle separation chip, with the aid of a meniscus generated by the relative movement; and
suctioning the sheath liquid using sheath liquid suction means and/or a suction device to thereby remove the microparticles to be removed, together with the sheath liquid from the microparticle separation chip.

Advantageous Effects of the Invention

The chip of the present invention has capture sites formed by pillars formed on a substrate, the microparticles to be captured, which are pressed downward by advection and aggregation, are captured in the capture sites, and the microparticles which have been removed pass through the pillar spacing and are removed to the exterior of the chip. Consequently, using the chip of the present invention makes it possible for a sample liquid to flow to the entire chip, and throughput for separating microparticles to be captured from the sample liquid can therefore be dramatically improved. Therefore, the present invention is capable of separating, with high precision in a short period of time, only low-content CTCs without pretreatment from whole blood containing, e.g., red blood cells, white blood cells, and the like. For example, CTCs can be efficiently separated out for a patient of early-stage cancer metastasis, patient follow-up after cancer treatment, or other cases of a patient sample having very few CTCs included in blood cells, and bedside cancer diagnosis is possible using a simple operation.

The chip used in the microparticle separation system of the present invention does not use anti-EpCAM antibodies, and therefore even CTC-negative or slightly positive tumor cells can be reliably detected. The chip of the present invention allows red blood cells, white blood cells, and other small-sized cells to flow to the exterior of the chip by way of the sheath liquid, is capable of capturing CTCs and other large-sized cells in capture sites provided to the channels, and is therefore capable of continuous processing without device clogging, which is different from conventional filter-type devices.

The chip used in the microparticle separation system of the present invention is capable of being mass produced using semiconductor formation processes, and the cost of a CTC examination can therefore be considerably reduced.

DESCRIPTION OF THE EMBODIMENTS

The microparticle separation chip, and the system and method for microparticle separation using the chip are described in detail below.

Figure 1:
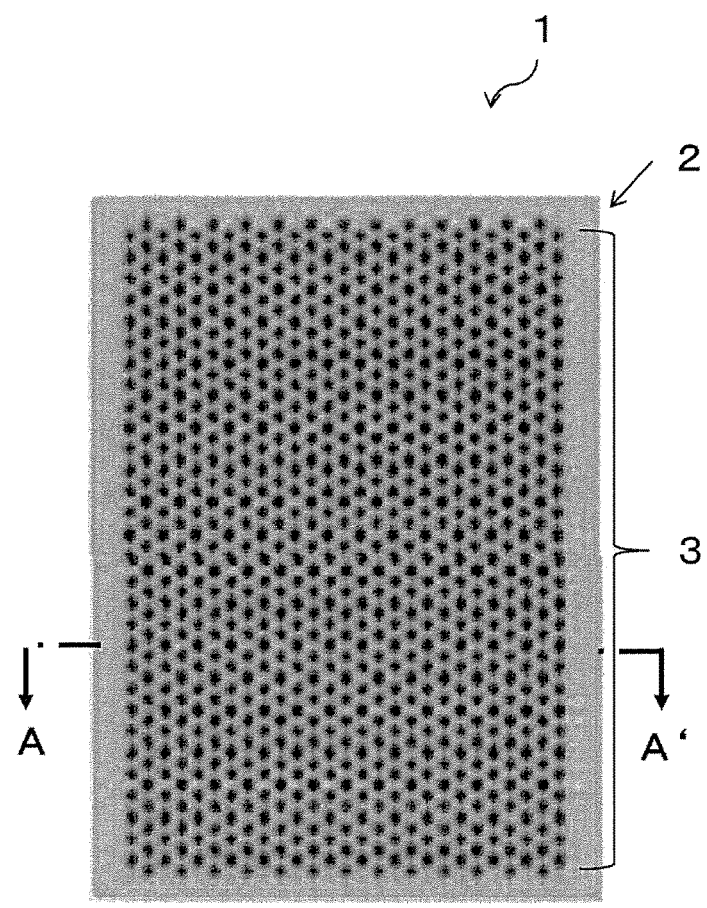
FIG. 1 is schematic view showing an example of the chip of the present invention.

FIG. 1 shows an example of the chip of the present invention, the chip 1 having a plurality of pillars 3 formed on a substrate 2, and has capture sites for capturing microparticles to be captured using at least three or more pillars. In the present invention, the term "pillar" refers to a column formed on the substrate 2. The term "microparticles" refers to particles that can be dispersed in a liquid, and the particle mode may a separated or aggregated state. The size of the microparticles is not particularly limited as long as the range allows the principles of a meniscus to be applied. The size can be about 1 mm or less.

Figure 2:
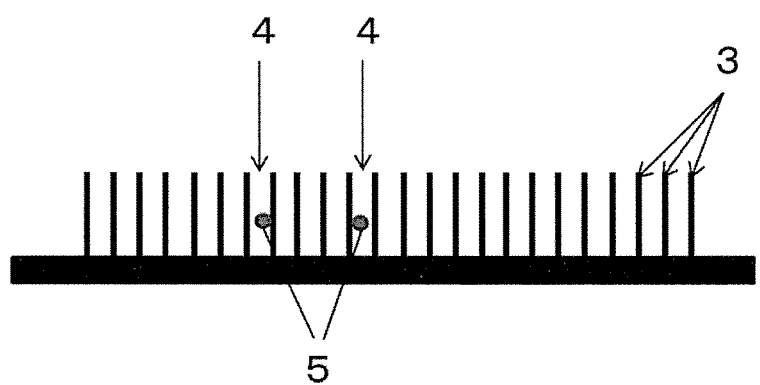
FIG. 2 is a view showing the cross section A-A' of FIG. 1.

FIG. 2 is a view showing the cross section A-A' of FIG. 1, one end of the pillars 3 being disposed on the substrate 2, and the other end being open above. A single capture site 4 is formed by at least three or more pillars 3. To-be-captured microparticles 5 pressed downward from the open side above the pillars 3 are captured in the capture site 4 by later-described advection and aggregation.

Figure 3:
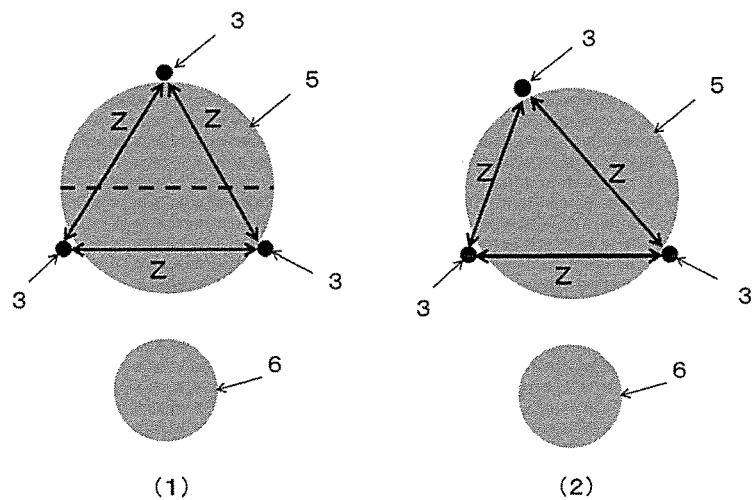
FIG. 3 is a view showing an example of a shape of the capture sites of the chip of the present invention.

FIG. 3 is a view showing an example of a shape of the capture sites 4 of the chip 1 of the present invention. FIG. 3(1) shows an example of the capture site 4 being formed using three pillars 3. The pillars 3 are formed so that the spacing Z of any mutually adjacent pillars which form a single capture site is $Y<Z \leq X$, where X is the size of the to-be-captured microparticles 5 and Y is the size of the microparticles 6 to be removed. In the present invention, the "spacing Z" refers to the shortest distance between the external periphery and the external periphery of any mutually adjacent pillars 3.

The spacing Z of the pillars 3 may be different, as shown in FIG. 3(2), and is not required to be the same as long as the relationship $Y<Z \leq X$ is satisfied. In the present invention, the "size" of the microparticles refers to the length in which the planar spacing is shortest when two parallel planes are disposed on both sides of the microparticles from any direction. For example, the size refers to the diameter when microparticles are spherical.

When the to-be-captured microparticles 5 are biological cells or other microparticles whose shape readily changes, it is possible that the cell will deform under fluid force and slip out between the pillars 3 in the capture sites 4. When the microparticles to be removed readily change shape in similar fashion, the microparticles 6 to be removed that have entered the capture site 4 can be drained from the capture site 4 even when the spacing of the pillars is narrower than the spacing of the microparticles 6 to be removed. Therefore, the spacing Z of any of the mutually adjacent pillars 3 can be suitably selected, as appropriate, in accordance with the shape-changing ratio of the to-be-captured microparticles 5 and/or the microparticles 6 to be removed. Examples of the spacing that can be adjusted, as appropriate, include $0.8Y<Z \leq 0.8X$, $Y<Z \leq 0.8X$, and $0.8Y<Z \leq X$.

Figure 4:
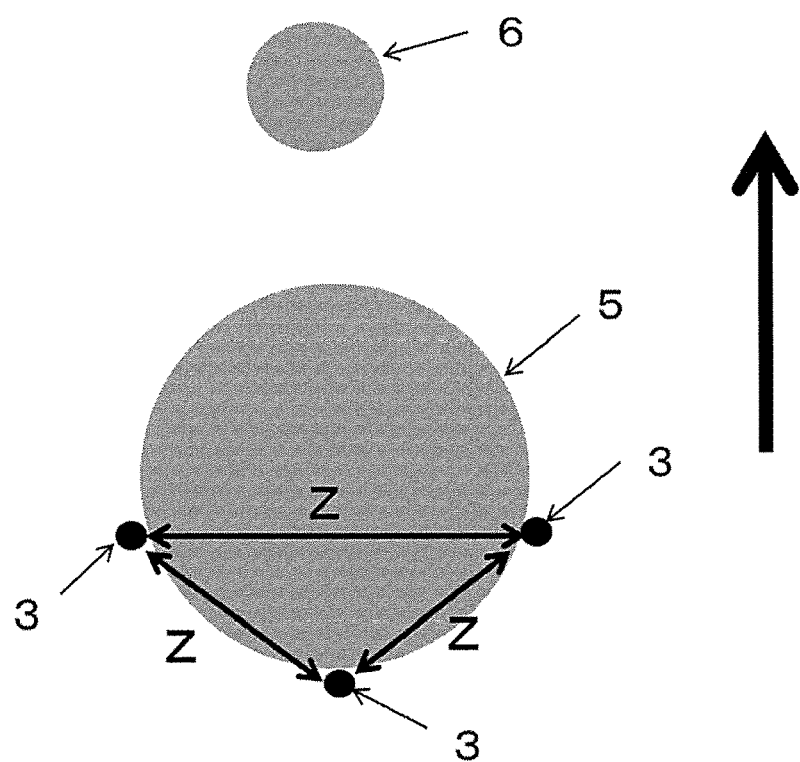
FIG. 4 is a view showing the positional relationship of the pillars 3 of a capture site 4 not included in the present invention.

In addition to the relationship $Y<Z \leq X$, the capture site 4 must be disposed in a positional relationship in which the to-be-captured microparticles 5 captured in the capture site 4 do not flow out from between any of the mutually adjacent pillars 3. FIG. 4 shows the positional relationship of the pillars 3 of a capture site 4 not included in the present invention. It is possible that the pillars 3 have captured only one portion of the to-be-captured microparticles 5, as shown in FIG. 4, even when the spacing Z of any of the mutually adjacent pillars 3 forming a single capture site 4 is formed so that $Y<Z \leq X$. In such a case, the sample liquid is suctioned the arrow direction shown in FIG. 4, whereupon the to-be-captured microparticles 5 captured in the capture site 4 flow out from the capture site 4. Therefore, as described above, the capture site 4 of the chip 1 of the present invention must be disposed in a positional relationship in which the captured to-be-captured microparticles 5 do not flow out from between any of the mutually adjacent pillars 3. Specifically, when the to-be-captured microparticles 5 have been sandwiched by two parallel planes from any direction and the microparticles are sectioned and placed in a plane so that the spacing of the planes includes the shortest line (the dotted line of the to-be-captured microparticles 5 in FIG. 3(1)), at least one pillar can be disposed on both sides at the boundary formed by the shorted lines.

The capture site 4 is not limited to a shape in which the pillars 3 are disposed so as to satisfy the relationship $Y<Z \leq X$ and a positional relationship in which the captured to-be-captured microparticles 5 do not flow out from between any of the mutually adjacent pillars 3, and examples of polygonal shapes that may be used include a quadrangle, pentagon, hexagon, heptagon, octagon, nonagon, and decagon. The polygon may or may not be an equilateral polygon.

Figure 5:
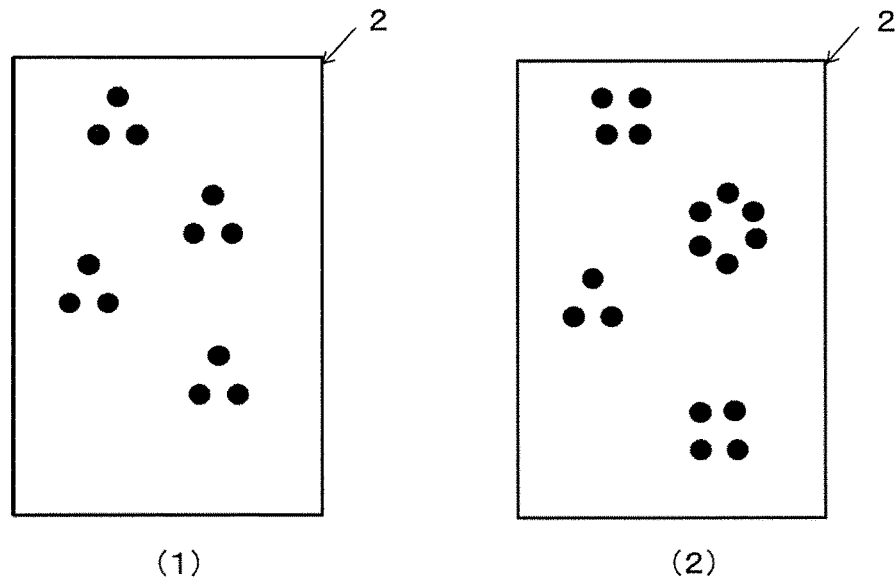
FIG. 5 is a view showing an example of an embodiment of the chip 1 of the present invention.

FIG. 5 is a view showing an example of an embodiment of the chip 1 of the present invention. A plurality of capture sites 4 having the same shape may be formed on the substrate 2, as shown in FIG. 5(1), or a plurality of capture site 4 having different shapes may be formed, as shown in FIG. 5(2). In the embodiment shown in FIG. 5(2), to-be-captured microparticles 5 having different sizes can be captured using a single chip 1.

When a plurality of capture sites 4 is formed, it is preferred that the capture sites 4 be adjacently disposed in order to efficiently capture the to-be-captured microparticles 5. When capture sites 4 are adjacently disposed, any capture site 4 and an adjacent capture site 4 will share a pillar 3, and is preferred that the capture sites 4 be in a continuous plane-filling state. In the present invention, the term "plane-filling state" refers to a state in which one or more limited types of polygon fill the plane without gaps. The "plane-filling state" is not particularly limited in shape as long as, in addition to the relationship $Y<Z \leq X$, a positional relationship is satisfied in which the to-be-captured microparticles 5 captured in the capture site 4 do not flow out from between any of the mutually adjacent pillars 3, as described above. Examples of a combination of a plurality of polygonal combinations include a combination of equilateral triangles and equilateral hexagons, a combination of equilateral triangles and quadrangles, and a combination of quadrangles and equilateral octagons. Combining polygons makes it possible to capture to-be-captured microparticles 5 of different sizes using a single chip 1.

Figure 6:
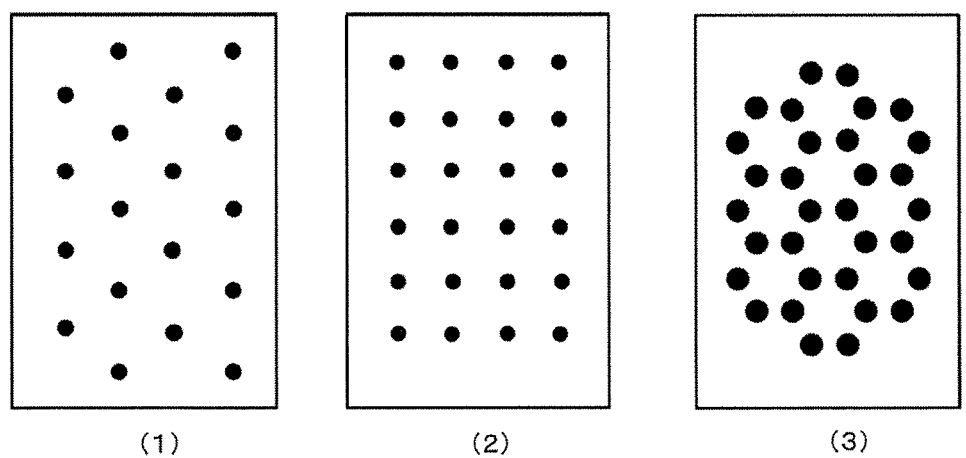
FIG. 6 shows an example of a capture site in which polygonal shapes of a single-type are arranged in a plane-filling state.

FIG. 6 shows an example of a capture site in which polygonal shapes of a single-type are arranged in a plane-filling state. FIG. 6(1) has equilateral triangles, FIG. 6(2) has quadrangles, and FIG. 6(3) has equilateral hexagons adjacently provided.

The cross-sectional shape of the pillars 3 is not particularly limited and may be selected, as appropriate, from a circle, polygon, or the like. The pillars 3 may be affixed onto the substrate 2, or first, a cast may be fabricated and the pillars then transferred to the material for the substrate to thereby efficiently fabricate the chip 1. When fabricated by transfer, the cross-sectional length (the diameter in the case of a circle; the length of the longest line among any line connecting the external periphery in the case of a polygon) of the pillars 3 is preferably 1 μm or more, and more preferably 2 μm or more due to reasons related to ease of machining and other reasons. The upper limit of the cross-sectional length of the pillars 3 is not particularly limited and may be determined, as appropriate, with consideration given to the spacing Z, which is determined by the size of the to-be-captured microparticles 5 and the microparticles 6 to be removed, and to the number of pillars 3 or the like that form the capture sites 4.

When CTCs are to be captured and red blood cells, white blood cells, and other blood cells other than CTCs are to be removed from whole blood, the spacing Z of the pillars 3 can be less than the diameter (15 to 30 μm) of the CTCs and greater than the diameter (about 7 μm) of red blood cells, white blood cells, and other blood cells. CTCs and blood cells readily change shape, as described above, and therefore the spacing Z of the pillars 3 can be about 6 to 12 μm. The spacing Z can be 6 to 24 μm when cancer cell aggregates (25 to 50 μm) are to be separated out from blood cells or mesothelial cells (about 7 to 15 μm) in peritoneal lavage liquids.

The height of the pillars 3 on the substrate 2 can be the height at which captured to-be-captured microparticles 5 do not flow out due to fluid-dynamic force of the sample liquid, and the height is preferably greater than 0.5 the size of the to-be-captured microparticles 5, more preferably the same size or greater. On the other hand, the upper limit of the height is not particularly limited, but it is difficult to insert a capillary to the vicinity of the substrate surface of the capture site 4 when the pillars 3 are too high, in the case that a sample liquid has been allowed to flow and the to-be-captured microparticles 5 captured in the capture sites 4 are thereafter suctioned and recovered using capillary force. Consequently, the height of the pillars 3 is preferably 10 times or less, more preferably double or less the size of the to-be-captured microparticles 5.

The chip 1 described above is an example of using a rectangle, but the shape is not particularly limited, and squares, hexagons, octagons, and other polygons may be used. As described below, the shape of the chip 1 is preferably circular when the chip 1 is rotated to generate advection and aggregation.

Figure 7:
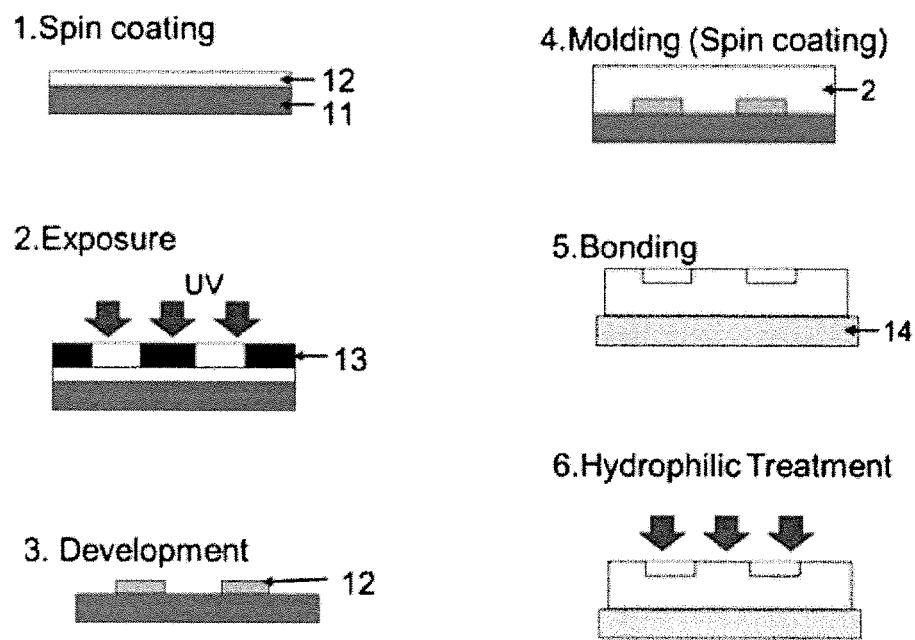
FIG. 7 is a flowchart showing an example of the procedure for fabricating the chip of the present invention.

The chip 1 can be fabricated using photolithographic techniques. FIG. 7 is a flowchart showing an example of the fabrication procedure 1. First, a substrate 11 for a template is organically washed by an ultrasonic washer, and then baked. A negative photoresist 12 is spin-coated on the substrate 11 and then prebaked on a hot plate.

2. The substrate is exposed using a photomask 13 having shapes for the capture sites 4.

3. The substrate is subjected to post-exposure baking on a hot plate, developed using development solution, and thereafter rinsed using ultrapure water. Moisture is dispersed using a spin drier or the like to dry and thereby fabricate a template. The spaces between convexities fabricated using the negative photoresist 12 on the substrate are portions that correspond to the pillars 3 after transfer.

4. The material for the substrate 2 of the chip 1 is allowed to flow onto the template.

5. The material for the substrate 2 to which the template pattern was transferred is separated from the template. The substrate 2 is bonded to a hard material 14 as required.

6. The surface of the substrate 2 is hydrophilized.

The organic washing is not particularly limited, and may be performed using acetone, ethanol, or other washing agent generally used in the field of semiconductor manufacturing. The substrate 11 for the template is not particularly limited as long as the material is generally used in the technical field of photolithography. Examples include silicon, silicon carbide, sapphire, gallium phosphide, gallium arsenide, gallium phosphide, and gallium nitride.

The negative photoresist 12 as well is not particularly limited as long as the material is generally used in the technical field of photolithography, and examples include SU-8, KMPR, and the like. If a positive photoresist is to be used in lieu of the negative photoresist 12, examples would include PMER, AZ, and the like. The resist removal liquid is not particularly limited and may be dimethyl formamide, acetone, or the like, as long as the removal liquid is generally used in the technical field of photolithography.

Examples of the material of the substrate 2 of the chip 1 of the present invention include polyethylene, polypropylene, polyvinyl chloride, polyvinylidene chloride, polystyrene, polyvinyl acetate, polytetrafluoroethylene, acrylonitrile butadiene styrene resin (ABS resin), AS resin, acrylic resin (PMMA), or other thermoplastic resin; and phenol resin, epoxy resin, melamine resin, urea resin, unsaturated polyester resin, alkyd resin, polyurethane, thermosetting polyimide, silicone rubber, or other thermosetting resin. When the to-be-captured microparticles 5 captured in the capture sites 4 are to be directly analyzed without recovery, the substrate 2 should be fabricated using a material that has optical transparency and lacks affinity with biomolecules. Examples include cyclo-olefin polymers (COP), polydimethylsiloxane (PDMS), polymethylmethacrylate (PMMA), polycarbonate (PC), plastics made of hard polyethylene or the like, and silicon or the like.

The chip 1 preferably has a thin substrate 2 for cases in which to-be-captured microparticles 5 are captured and thereafter observed using a microscope or the like. However, if the substrate 2 is excessively thin, it may be difficult to move the chip 1 in cases where the chip 1 is to be moved. Therefore, the chip 1 can include a hard material 14. Examples of the hard material 14 include glass, plastic, and silicon, and these can be affixed to the substrate 2.

Hydrophilizing the surface of the chip 1 makes it possible to prevent air bubbles from entering the grooves when liquid is injected. Examples of the hydrophilizing treatment include plasma treatment, surfactant treatment, PVP (polyvinyl pyrrolidone) treatment, and photocatalytic treatment. For example, subjecting the surface of the chip 1 to a plasma treatment for 10 to 30 seconds makes it possible to introduce a hydroxyl group to the surface.

Described next are the microparticle separation system using the chip 1 and the method for microparticle separation using the microparticle separation system.

Figure 8:
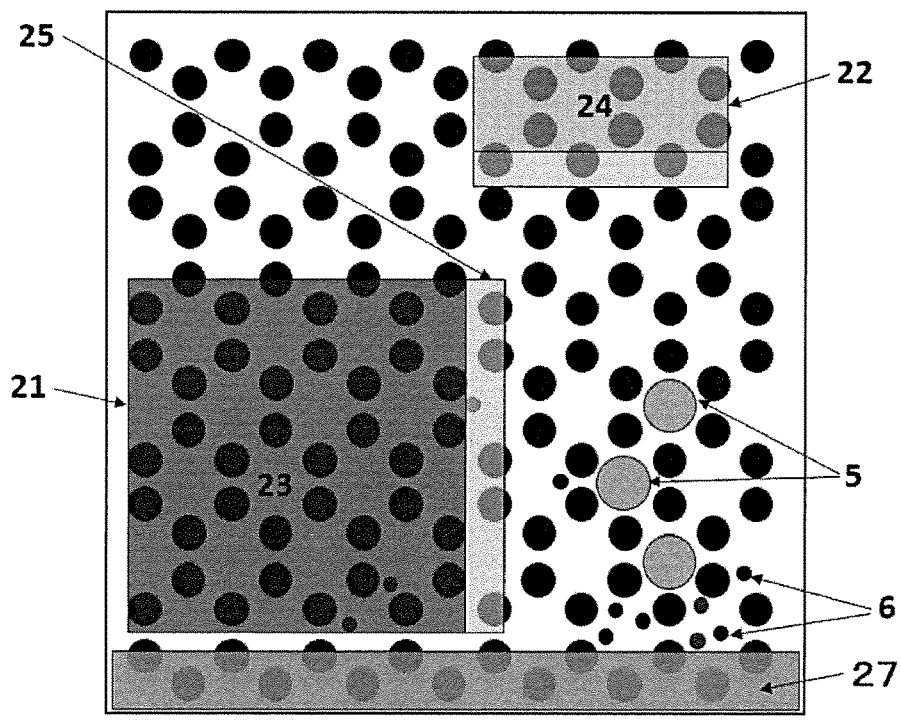
FIG. 8 shows an outline of the system and method for microparticle separation of the present invention.

FIG. 8 shows an outline of the system and method for microparticle separation of the present invention, and shows an embodiment for causing the chip 1, and the thin plate for a sample liquid and thin plate for a sheath liquid to move in relative fashion to thereby generate a meniscus. The microparticle separation system of the present embodiment includes the chip 1, a thin plate 21 for a sample liquid, a thin plate 22 for a sheath liquid, and a suction means and/or suction device (not shown) for suctioning the sheath liquid. The suction means and/or suction device is disposed in contact with the external peripheral side 27 of the chip 1 that is parallel to the direction of movement of the thin plate 22 for a sheath liquid, and can suction the sheath liquid from above the pillars 3.

The thin plate 21 for a sample liquid and the thin plate 22 for a sheath liquid may be glass, plastic, or the like and are not particularly limited as long as these do not react with the sample liquid or sheath liquid. The sheath liquid is not particularly limited as long as the microparticles to be separated out are not damaged or otherwise compromised. When whole blood is used as a sample, the sheath liquid may be a phosphate-buffered saline (PBS), a Tris buffer or various other buffer solutions, a simulated body fluid (SBF), a general cell culture medium, or other generally used sheath liquids may be used, though no particular limitation is imposed thereby.

FIG. 8 shows an example in which whole blood is used as the sample, and CTC5s are captured from the whole blood. Whole blood 23 is injected between the chip 1 and the thin plate 21 for a sample liquid, and the chip 1 and the thin plate 21 for a sample liquid are moved in relative fashion to thereby generate a meniscus 25.

Figure 9:
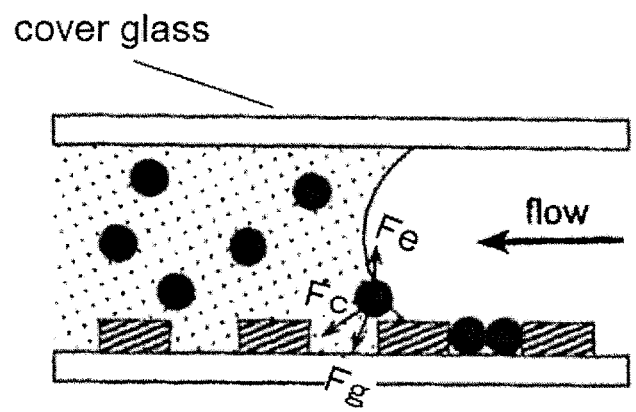
FIG. 9 illustrates the principle for generating a meniscus.

FIG. 9 is a view illustrating the principle for generating a meniscus. In the present invention, a technique is used in which the microparticles are arrayed in a closely packed structure with each other using capillary force (lateral capillary force in particular) between microparticles present in the air-liquid boundary, which is referred to as the advection-aggregation method. When a meniscus composed of a suspension liquid in which microparticles are dispersed in a solution is formed on a substrate, locations in which microparticles partially emerge from the solution are formed at the leading edge of the meniscus as shown in the drawing. In locations of partial emergence, a downward-pressing force (Fg among Fe, Fc and Fg shown in FIG. 9) produced by gravity and boundary tension is imparted to the microparticles as they move together with the meniscus.

CTCs, which are the to-be-captured microparticles 5, are pressed downward by the above-described meniscus principle, and are thereby dropped into and captured by the capture site open at the top. Meanwhile, blood cells, which are microparticles 6 to be removed, pass between the pillars 3 by the suction force of the later-described suction means and/or suction device and are drained from the chip 1. Also, the sheath liquid also generates a meniscus in the same manner, whereby the sheath liquid readily enters onto the substrate 2 from between the pillars 3.

The gap between the chip 1, and the thin plate 21 for a sample liquid and thin plate 22 for a sheath liquid is preferably 200 to 1000 μm. When the gap is less than 200 μm, the amount of sample liquid to be introduced is reduced and the processing capability is reduced, and when the gap is greater than 1000 μm, the meniscus force is reduced and adequate separation cannot be obtained. The gap can be adjusted using a microstage. The relative movement speed between the chip 1, and the thin plate 21 for a sample liquid and thin plate 22 for a sheath liquid is preferably 20 to 50 μm/s. When the speed is less than 20 μm/s, the processing time is lengthened and processing capability is reduced; and when the speed is greater than 50 μm/s, microparticles are not captured and separation efficiency is reduced.

The flow rate of the sheath liquid is preferably 20 to 4500 µm/s. The flow rate of the sheath liquid varies in accordance with the spacing between the pillars and is more rapid as a location narrows. In the present invention, the term "flow rate of the sheath liquid" is the flow rate of liquid that flows between pillars and refers to the maximum flow rate. When the flow rate is less 20 µm/s, the separation efficiency is reduced due to a reduced ability to wash away blood cells, and when the flow rate is greater than 4500 µm/s, any temporarily captured CTCs are suctioned away and separation efficiency is reduced. The flow rate of the sheath liquid can be adjusted using the suction force of the suction means and/or suction device. The suction device can be a suction pump, a micro-syringe, or the like, and is not particularly limited as long as a liquid can be suctioned. The example shown in FIG. 8 is a scheme in which the sheath liquid 24 is injected as required between the chip and the thin plate 22 for a sheath liquid, but it is also possible to connect the sheath liquid container or a tube or the like extending from the sheath liquid container to one end of the thin plate 22 for a sheath liquid to thereby allow sheath liquid to be automatically fed.

Figure 10:
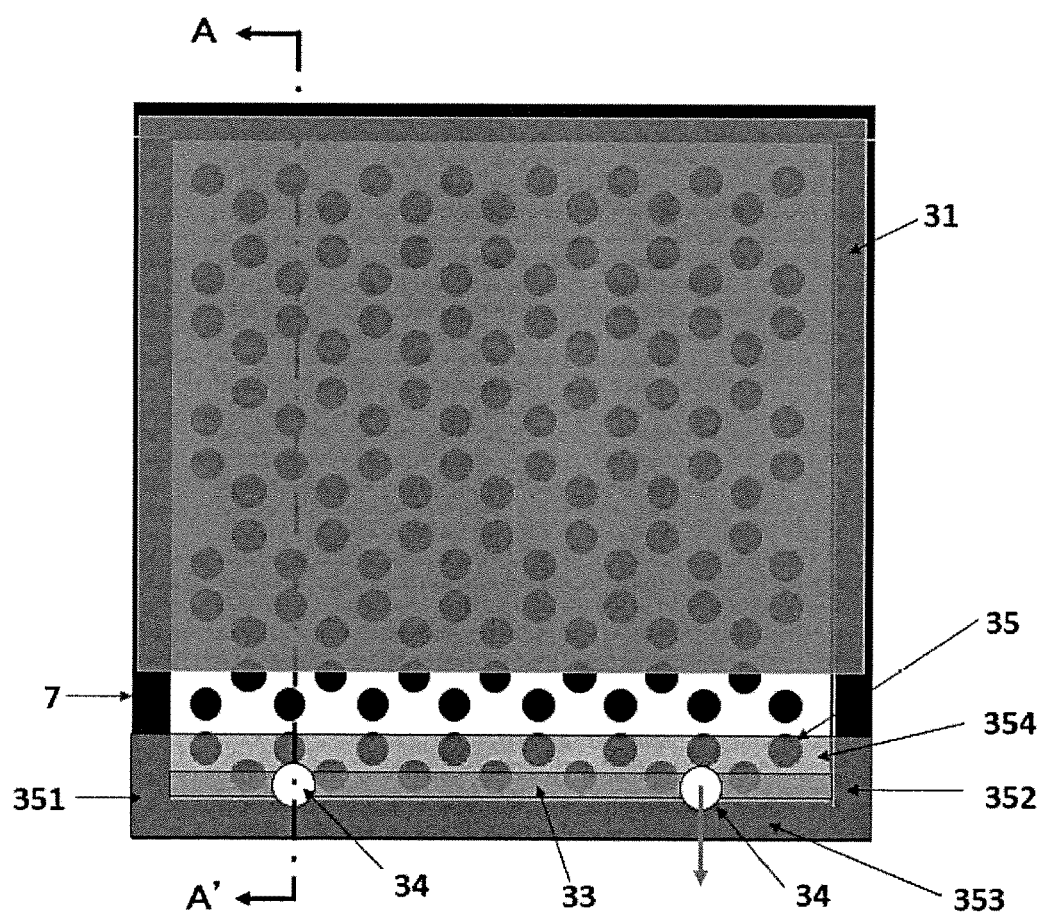
FIG. 10 shows an outline of another embodiment of the system and method for microparticle separation of the present invention.

FIG. 10 shows an outline of another embodiment of the system and method for microparticle separation of the present invention, and an embodiment for suctioning a sample liquid without causing the chip 1 for microparticle separation and the cover plate to move in relative fashion to thereby generate a meniscus. The microparticle separation system of the present embodiment comprises at least: a chip 1; a cover plate 31 overlaid on the chip 1, the sample liquid and sheath liquid being suctioned to thereby generate a meniscus; and suction means and/or a suction device (not shown). The embodiment shown in FIG. 10 is an example in which a stepped part 7 having the same height as the pillars 3 is formed at the external periphery of the chip 1, and the sample liquid and sheath liquid are suctioned by the suction means and/or suction device via a suction unit 35 having a lateral groove 33 and a suction hole 34 that is in communication with the lateral groove 33, which is formed in the lengthwise direction and is capable of suctioning the sample liquid and the sheath liquid by capillary force. Forming a stepped part 7 makes it possible to bring both ends 351 and 352 as well as one side surface 353 of the suction unit 35 into contact with the stepped part 7, and therefore make it possible for the sample liquid and the sheath liquid to be suctioned from the other side surface 354 without entry of air bubbles or the like. A planar section in which the pillars 3 are not formed at the external periphery of the chip 1 is provided, and the sample liquid and sheath liquid can be suctioned from the planar section using the suction means and/or suction device.

In the present embodiment, the sample liquid is suctioned using suction means and/or a suction device to thereby separate out the microparticles contained in the sample liquid, and it is not therefore essential that the sheath liquid flow after the sample liquid has flowed because the sample liquid itself serves as a sheath liquid if a diluted sample liquid is used. When the to-be-captured microparticles are to be separated with high purity, it is possible to select whether to use a sheath liquid in accordance with the object of separation, such as washing away remaining microparticles to be removed by allowing a sheath liquid to flow.

Figure 11:
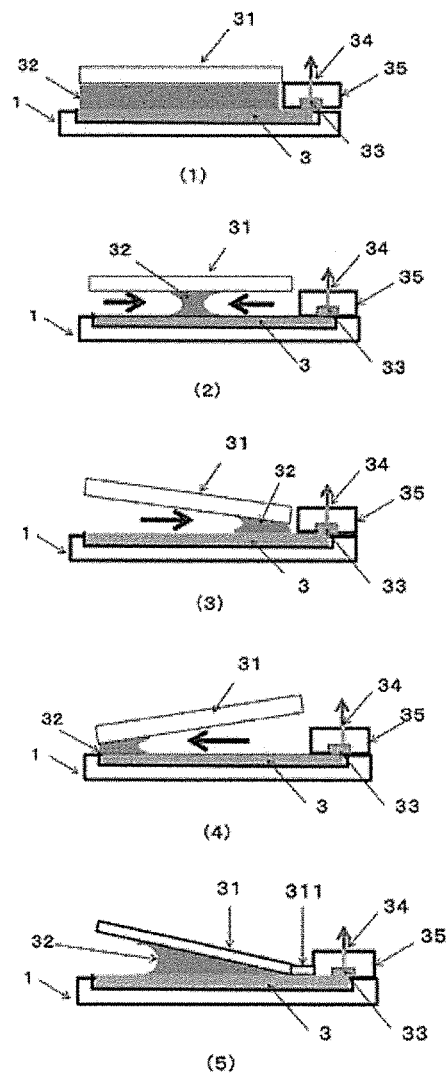
FIG. 11 is a view showing the cross section A-A' of FIG. 10.

FIG. 11 is a view showing the cross section A-A' of FIG. 10, and is a view illustrating the principle for generating a meniscus in the present embodiment. When a sample liquid and a sheath liquid 32 are injected between the chip 1 and the cover plate 31 and suctioned by suction means and/or a suction device (not shown), as shown in FIG. 11(1), the sample liquid and the sheath liquid pass between the pillars 3 and are drained from the suction unit 35. In this process, a capillary force is generated in the sample liquid and the sheath liquid 32 between the chip 1 for and the cover plate 31, and a meniscus is therefore generated in the manner shown in FIG. 11(2).

The movement direction of the sample liquid and the sheath liquid 32, shown in FIG. 11(2) is shown for the case in which the cover plate 31 is arranged parallel to the chip 1, and, for example, when the cover plate 31 on the suction unit 35 side is arranged with a slope so as to be closer to the chip 1, as shown in FIG. 11(3), the sample liquid and the sheath liquid 32 move toward the suction unit 35 side due to the pressure applied to the sample liquid and the sheath liquid 32. Conversely, the sample liquid and the sheath liquid 32 move to the opposite side from the suction unit 35 due to the pressure applied to the sample liquid and the sheath liquid 32 when the cover plate 31 on the opposite side of the suction unit 35 is arranged with a slope so as to be closer to the chip 1, as shown in FIG. 11(4). The present invention can be implemented in any of the embodiments of FIGS. 11(2) to (4), but the embodiment shown in FIG. 11(3) is preferred in that the sample liquid and the sheath liquid 32 are closer to the suction unit 35 side and the suction force of the suction means and/or a suction device can therefore be reduced. The gap between the chip 1 and the cover plate 31 is preferably 200 to 1000 µm in the same manner as the thin plate 21 for a sample liquid described above, and adjustment can be made within the range of this gap using a microstage. In the case that the cover plate 31 is sloped, the degree of slope is preferably about 6° to 18°. When the slope angle is less than 6°, the pressure applied to the sample liquid and the sheath liquid is insufficient; and a slope angle greater than 18° is too great to obtain a meniscus angle that would be effective for capturing microparticles, which is not preferred. The embodiment shown in FIG. 11(5) has a second cover plate 311 so that the meniscus of the sample liquid and the sheath liquid 32 is not generated on the suction side, and since a closed channel system can be configured, it is possible to provide stable suctioning.

The cover plate 31 and the second cover plate 311 can be fabricated using the same material as the thin plate 21 for a sample liquid described above. The size of the cover plate 31 is not particularly limited, but in the present embodiment, a meniscus can be generated without moving the cover plate 31. Therefore, in order to improve processing efficiency, it is desirable for the cover plate to be formed to a size that allows all the pillars 3 formed in the chip 1 to be covered. In relation to the size of the second cover plate 311, the length in the lateral direction can be the same length as the cover plate 31 and the width can be adjusted, as appropriate, in a range in which a meniscus is not generated.

The embodiment shown in FIG. 11 is an example of a quadrangular chip 1, but the chip 1 is not limited to being a quadrangle, and may also be a pentagon, hexagon, or other polygon or may be a circle. The embodiment shown in FIG. 11 has the suction unit 35 disposed to one side of the outer side of the chip 1, but the suction unit 35 may be disposed at the external periphery of a polygonal or circular chip 1, the cover plate 31 may be polygonal or circular, and the injection hole of the sample liquid and the sheath liquid 32 is formed in the center of the cover plate 31, whereby advection and aggregation can be generated so as to draw the sample liquid and the sheath liquid 32 injected in the center of the chip 1 to the external periphery of the chip 1. Furthermore, conversely to the embodiment described above, the cover plate can be essentially ring-shaped to cover the external periphery of a polygonal shape or the external peripheral portion of a circular shape, a polygonal or circular suction unit 35 can be disposed in the center of the essentially ring-shaped cover plate, and advection and aggregation can be generated so as to draw the sample liquid and sheath liquid 32 injected from the external peripheral portion of the chip 1 to the center of the chip 1. A preferred case is to generate a meniscus so as to draw to the center of the chip 1, whereupon the distance of the surface at which the meniscus is generated is made longer, and the sample processing efficiency is improved.

Examples of means for suctioning the sample liquid and the sheath liquid 32 include a fabric, cotton, sponge, chamois, or other suctioning pad, and the suction pad can be placed in direct contact with the upper part of the pillars 3 of the chip 1 or the planar section in which the pillars 3 are not formed to suction/drain the sample liquid and sheath liquid 32. Suctioning/draining the sample liquid and the sheath liquid 32 may be carried out via the suction unit 35.

Figure 12:
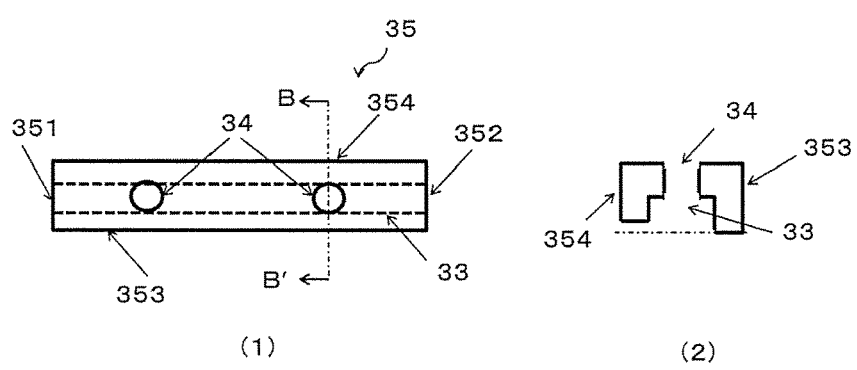
FIG. 12 shows an outline of the suction unit.

FIG. 12 shows an example of an embodiment of the suction unit 35 when contact is made with the planar section in which the pillars 3 are not formed, FIG. 12(1) is a top view showing an outline of the suction unit 35, and FIG. 12(2) shows a cross section along the line B-B' of the suction unit 35. The width of the lateral groove 33 must be such that at least removed microparticles are allowed to pass. Since at least the removed microparticles must be allowed to pass, the width of the lateral groove 33 is preferably at least 8 μm or more when the sample is whole blood, and more preferably 10 μm or more in order to increase processing capability. On the other hand, the width of the lateral groove 33 does not have a particular upper limit as long as capillary force is generated, and the upper limit can be adjusted, as appropriate, with consideration given to the amount of sample liquid and sheath liquid to be suctioned, the capillary force, and the like. For example, a width of about 200 μm can be provided. A gap must be produced when the suction unit 35 is brought into contact with the planar section in order for the sample liquid and the sheath liquid to be suctioned into the lateral groove 33. Accordingly, among both ends 351 and 352 of the suction unit 35 as well as the side surfaces 353 and 354 sandwiching the lateral groove 33, it is possible to make the height of the side surface 353 on the side opposite from the pillars 3 to be the same when contact is made with the planar section 7, and to make only the side surface 354 disposed on the pillars 3 side to be shorter than the end part 351, the end part 352, and the side surface 353. The difference between the side surfaces 353 and 354 is preferably, in similar fashion to the width of the lateral groove 33, 8 μm or more, more preferably 10 μm. The upper limit of the difference is not particularly limited as long as a capillary force can be generated, and can be adjusted, as appropriate, with consideration given to the amount of sheath liquid to be suctioned and/or the capillary force, and the like. For example, a difference of about 200 μm can be provided. When a stepped part 7 is provided to the chip 1, the height of the side surfaces 353 and 354 can be made to be the same, as shown in FIG. 10. The sample liquid and the sheath liquid 32 suctioned into the lateral groove 33 can be suctioned/drained through the suction hole 34 using a pump, micro-syringe, or other suction device. When the amount of sample liquid and sheath liquid to be drained is considerable and cannot be suctioned out using only the lateral groove 33, it is also possible to use a suction device in combination with the lateral groove. The number of suction holes 34 is not particularly limited, and it is possible to provide a number sufficient to ensure no considerable difference in the flow rate of the sample liquid and sheath liquid 32 that flow between the pillars 3 formed on the substrate 2.

The width of the lateral groove 33 may be increased and the above-noted fabric, cotton, sponge, chamois, or other suction means inserted into the lateral groove 33, and the sample liquid and the sheath liquid 32 absorbed into the suction means can be suctioned by a suction device through the suction hole 34. In the present embodiment, the flow rate of the sample liquid and the sheath liquid flowing between the pillars 3 is adjusted by the suction force of the suction means and/or a suction device. Accordingly, the speed at which the sample liquid and the sheath liquid are suctioned can be more stably maintained by furthermore suctioning the sample liquid and sheath liquid suctioned to the suction means by a suction device in comparison with merely suctioning the sample liquid and the sheath liquid 32 by suction means or suctioning the sample liquid and the sheath liquid 32 into the lateral groove 33 by capillary force. The suction device and suction hole 34 can be connected using a tube composed of silicone or the like.

The material constituting the suction unit 35 is not particularly limited and may be acrylic, nylon, Teflon (registered trademark), or other resin, or glass or the like, as long as it does not react with the sample liquid or the sheath liquid. The suction unit 35 can be fabricated by cutting using a drill, end mill, or other cutting tool, or by fabricating a mold in the shape of the suction unit 35 and using injection molding.

The microparticle separation system of the present embodiment is capable of trapping CTCs in, e.g., a blood sample in the capture sites and washing away the other blood cells and the like together with the sheath liquid by first inserting a sample liquid between the chip 1 and the cover plate 31, suctioning the sample liquid using suction means and/or a suction device, and then inserting a sheath liquid as required between the chip 1 and the cover plate 31 and suctioning the sheath liquid. The sample liquid or sheath liquid inserted between the chip 1 and the cover plate 31 may be injected between the chip 1 and the cover plate 31 using a syringe or the like, or a hole may be provided to the cover plate 31 and the sample liquid and the sheath liquid may be injected through the hole.

The flow rate of the sample liquid and the sheath liquid 32 is preferably 20 to 4500 μm/s. When the flow rate is less than 20 μm/s, the separation efficiency is reduced due to a reduced ability to separate and wash away blood cells, and when the flow rate is greater than 4500 μm/s, any temporarily captured CTCs are suctioned away and separation efficiency is reduced. The flow rate of the sample liquid and the sheath liquid can be adjusted using the suction force of the suction means and/or suction device.

In the present embodiment, a sheath liquid is allowed flow as required after the sample liquid has first been allowed to flow. Therefore, considerable suction force is required when whole blood or another sample liquid with high viscosity is to be suctioned without aid. Accordingly, when blood is used as the sample liquid, the sample liquid may be diluted 2 to 10 times using a sheath liquid or the like, preferably about 3 to 5 times. In the present embodiment, the position in which a meniscus is generated is not varied together with relative movement, but rather, a meniscus can be generated in all the portions where the chip 1 and the cover plate 31 overlap, and since suctioning the sample liquid and the sheath liquid allows the position at which a meniscus is generated to be moved, the time required for separation can therefore be sufficiently reduced even when whole blood has been diluted.

Figure 13:
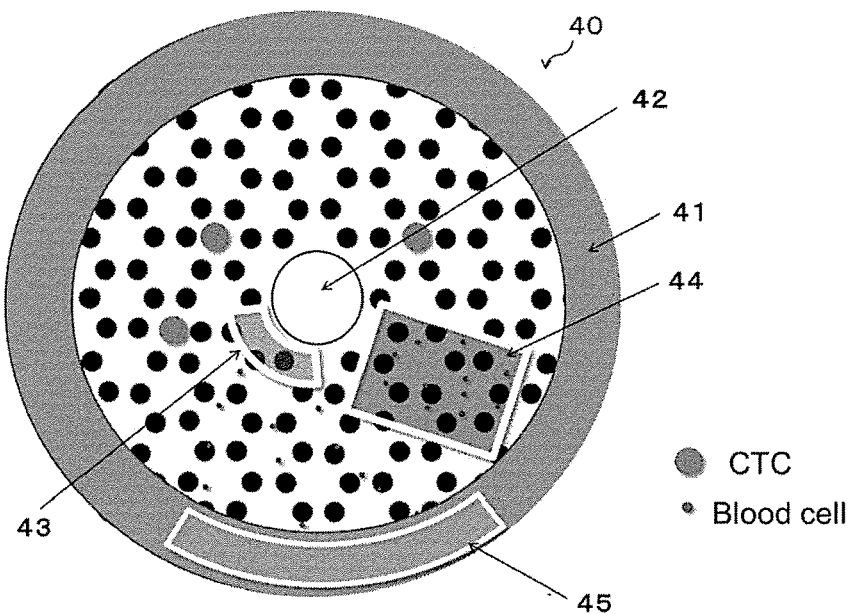
FIG. 13 shows another embodiment of the microparticle separation system of the present invention.

FIG. 13 shows another embodiment of the microparticle separation system of the present invention. The present embodiment shows an example of using a circular chip 40, but there is no particularly limitation to a polygonal shape or other shape as long as the chip can be mounted on and rotated by later-described rotation means of the microparticle separation system. The chip 1 used in the present embodiment has a planar section 41 in which pillars 3 are not formed in the external peripheral portion, and is capable of being in contact with suction means and/or a suction device. Center holes 42 may be provided in the center portion, as required, to allow for mounting on the rotation means.

In the present embodiment, a meniscus is generated in the sheath liquid in an area 43 corresponding to the planar section for sheath liquid advection and aggregation (may hereinafter be described as "sheath liquid planar section") of a later-described advection-aggregation unit, and a meniscus is generated in the sample in an area 44 on the external peripheral side from the area for generating a meniscus in the sheath liquid, and corresponds to the planar section for sample advection and aggregation (may hereinafter be described as "sample planar section"). The sample liquid and the sheath liquid can be drained from an area 45 that corresponds to a hole of the advection-aggregation unit.

Figure 14:
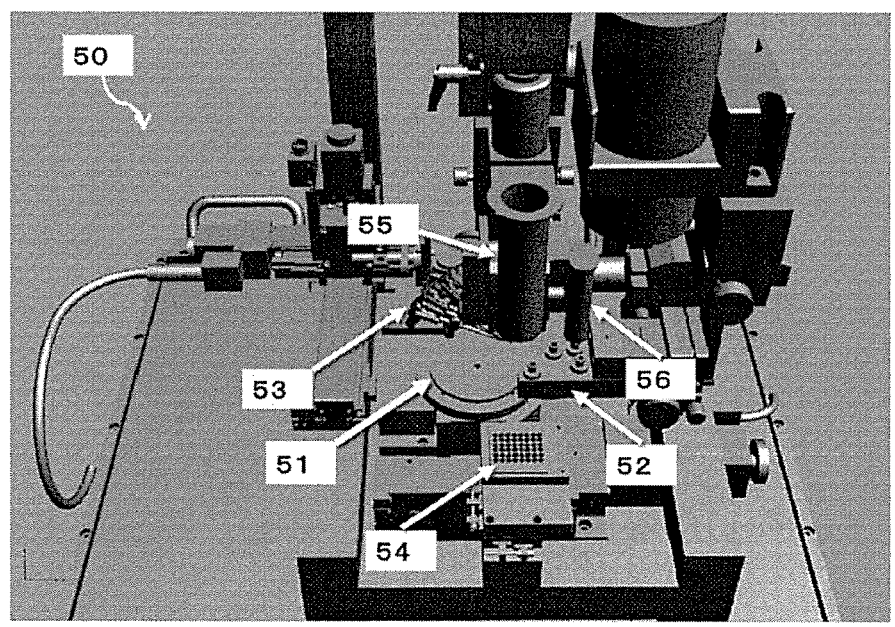
FIG. 14 shows an image of the entire microparticle separation system of the embodiment shown in FIG. 13.

FIG. 14 shows an image of the entire microparticle separation system of the embodiment shown in FIG. 13, and is a view showing an outline of the system 50 for microparticle separation using the circular chip 40. The system may include at least rotation means 51 for mounting and rotating the chip 40, an advection-aggregation unit 52, and sheath liquid suction means and/or suction device (not shown), and may also include microparticle extraction means 53 when microparticles captured in a capture site are to be extracted. PCR means 54 may be included when the captured microparticles are a biological material containing nucleic acid and PCR is to be carried out after separation. FIG. 14 shows an example provided with wells that are used in PCR. It is also possible to provide sheath liquid injection 55 for feeding sheath liquid to a sheath liquid injection port and sample injection for feeding a sample to a sample injection port of the later-described advection-aggregation unit. The sheath liquid injection 55 and the sample injection 56 are not particularly limited as long as they are capable of feeding liquid, examples being manual liquid feeding using a syringe or the like, and a commercial constant-flow pump or the like. The liquids may be dropped by gravity from a bottle or the like without the imparting force to the liquid feeding, and in such a case, a clamp used for regulating titration flow rate may be provided to regulate the flow rate.

The rotation means 51 is not particularly limited as long as the chip 40 can be mounted and rotated. An example is to provide a motor or other drive means under a rotatable disk on which the chip 40 can be mounted and to rotate the disc. The size of the meniscus to be generated is preferably fixed, and the drive means is therefore preferably capable of being kept at a constant speed.

Figure 15:
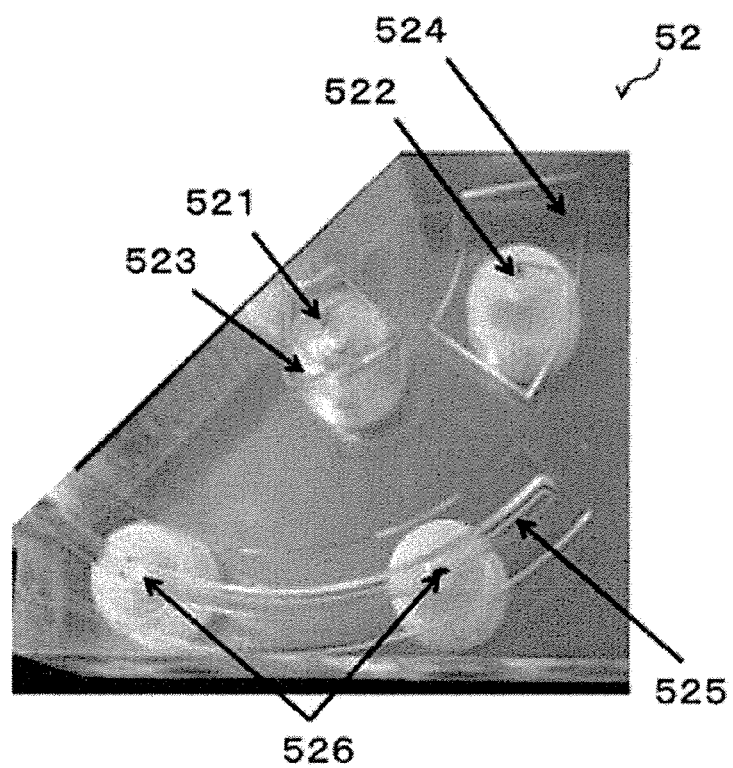
FIG. 15 is a photograph in place of a drawing showing an outline of the advection-aggregation unit.

FIG. 15 is a photograph showing an outline of the advection-aggregation unit 52. The advection-aggregation unit 52 has formed therein at least a sheath liquid injection port 521, a sample injection port 522, a sheath liquid planar section 523, and a sample planar section 524. The advection-aggregation unit 52 may be provided with a hole 525 for mounting a sheath liquid suction pad or for suctioning sheath liquid by capillary force, and a sheath liquid suction port 526 to provide communication with the hole 525 and connect to the sheath liquid suction device (not shown). The sheath liquid planar section 523 and the sample planar section 524 are preferably planar shaped on the surface facing the chip 40 in order to generate a meniscus by relative movement with the chip 40. A meniscus is generated between the chip 40, and the sheath liquid planar section 523 and sample planar section 524, and since a meniscus is not required to be formed in locations other than the sheath liquid planar section 523 and the sample planar section 524, the sheath liquid planar section 523 and the sample planar section 524 of the advection-aggregation unit must be provided with a stepped part that is thicker than other portions. Meanwhile, in relation to the hole 525, when a sheath liquid suction pad is mounted on the hole 525, the protruding distance from the hole 525 in which the sheath liquid suction pad is mounted can be adjusted so that the sheath liquid suction pad makes contact with the sheath liquid. Therefore, the hole 525 can be formed in the same surface as the other portions, the planar section in which the hole 525 is to be provided can be formed in a position that is at the same height as the sheath liquid planar section 523 and the sample planar section 524, and the hole 525 can be formed in the planar section. When the hole 525 is used as a hole for suctioning the sheath liquid by capillary force, the planar section in which the hole 525 is formed may be formed more thickly than the sheath liquid planar section 523 and sample planar section 524 to form a gap that allows the sheath liquid to be suctioned from the planar section 41 by capillary force. The number and position of sheath liquid suction ports 526 to be formed are not particularly limited as long as communication is provided to the hole 525, and can be adjusted, as appropriate.

The sheath liquid injection port 521 can be formed in the sheath liquid planar section 523 and the sample injection port 522 can be formed in the sample planar section 524, as shown in FIG. 15, and the sheath liquid injection port 521 can be formed on the upstream side of the sheath liquid planar section 523 and the sample injection port 522 can be formed on the upstream side of the sample planar section 524 when the advection-aggregation unit 52 and the chip 40 are to be moved in relative fashion. The sheath liquid flows in the direction of the planar section 1 from a center hole 42, and therefore the shape and size of the sheath liquid planar section 523 is not particularly limited as long as it can be formed near the center hole 42. Meanwhile, the shape of the sample planar section 524 is not particularly limited as long as a meniscus line is generated on the capture site 4, and it is preferred that the shape and size be such that a meniscus line is generated from the center hole 42 to the capture site 4 adjacent to the planar section 41 in order to efficiently capture to-be-captured microparticles 5.

Figure 16:
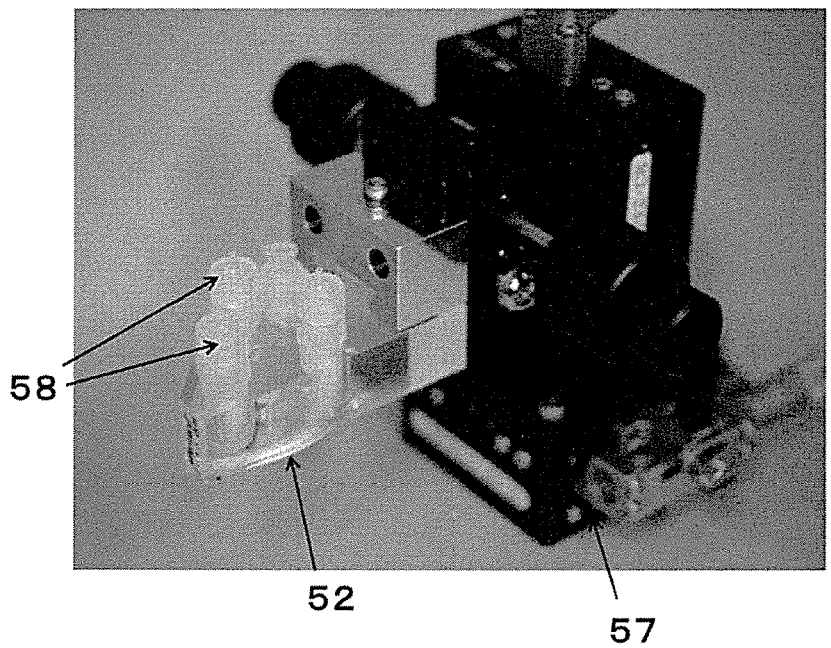
FIG. 16 is a photograph in place of a drawing showing an enlarged perspective view of the advection-aggregation unit.

FIG. 16 is a photograph showing an enlarged perspective view of the advection-aggregation unit 52, and the advection-aggregation unit 52 is attached to height-adjustment means 57 for maintaining a gap with the chip 40 mounted on the rotation means 51. The height-adjustment means 57 is not particularly limited as long as the height of the advection-aggregation unit 52 can be adjusted using a screw or the like. The sheath liquid planar section 523 and the sample planar section 524 of the advection-aggregation unit 52 is disposed so as to be positioned 200 to 1000 μm away from the pillars 3 of the chip 40. When the gap between the pillars 3 and the sheath liquid planar section 523 and sample planar section 524 of the advection-aggregation unit 52 is less than 200 μm, the amount of sample liquid that can be introduced is restricted and processing capacity is reduced, and when the gap is greater than 1000 μm, the meniscus force is reduced and sufficient separation cannot be obtained. When a advection-aggregation unit 52 is to be used, the sheath liquid injection port 521 can be connected to the sheath liquid injection 55, the sample injection port 522 can be connected to the sample injection 56, and the sheath liquid suction port 526 can be connected to the sample liquid suction device (not shown), via a tube 58 composed of silicone or the like.

The sample liquid suction means is not particularly limited as long as contact can be made with the planar section of the chip 40 and the sheath liquid can be suctioned. Examples of the sheath-liquid-suctioning pad include a fabric, cotton, sponge, and chamois, which can suction the sheath liquid via direct contact or by contact with the planar section 41 via the hole 525 in the advection-aggregation unit 52.

In lieu of inserting a sheath-liquid-suctioning pad into the hole 525, the width of the hole 525 can be adjusted to a width at which capillary force is generated, and the sheath liquid can be suctioned by capillary force by bringing the hole 525 into contact with the planar section 41. In such a case, the width of the hole 525 must allow at least the removed microparticles to pass together with the sheath liquid, and is therefore preferably at least 8 μm or more when the sample is whole blood, and 10 μm or more in order to increase processing capability. The upper limit of the width of the hole 525 is not particularly limited as long as capillary force can be generated. The width can be adjusted with consideration given to the amount of sample liquid to be suctioned, the capillary force, and the like. For example, a width of about 200 μm can be provided. A gap must be produced when the hole 525 is brought into contact with the planar section 41 in order for the sample liquid and the sheath liquid to be suctioned into the hole 525. Accordingly, it is possible make the height of the side surface on the side opposite from the pillars 3 to be the same when contact is made with the planar section 41 and the both ends of the hole 525, and to make only the side surface disposed on the pillars 3 side of the hole 525 to be shorter than the other portions. The height difference is preferably 8 μm or more, more preferably 10 μm or more. The upper limit of the difference is not particularly limited as long as a capillary force can be generated, and can be adjusted, as appropriate, with consideration given to the amount of sheath liquid to be suctioned and/or the capillary force, and the like; a difference of, e.g., 200 μm may be provided. The chip 40 is not limited to the embodiment described above, and, for example, it is possible to provide a stepped part 7 as shown in FIG. 10, and to have the hole 525 of the advection-aggregation unit 52 disposed on the pillars 3 side. In lieu of the planar section 41, it is possible to provide a groove section that is lower than the surface of the substrate 2, and to adjust the advection-aggregation unit so that the size and arrangement allow the sample liquid and sheath liquid to be suctioned from the groove section.

The sample liquid may be suctioned using the suction means described by example above, or a suction pump or other suction device, and the suction port connected to the suction device may be brought into contact with the planar section 41 to suction the sheath liquid. In the present invention, the flow rate of the sheath liquid 32 is adjusted by the suction force of the sheath-liquid-suctioning means regardless of the shape of the chip 40. Consequently, when the amount of sample liquid and sheath liquid used for microparticle separation is considerable, and the sheath liquid suction pad or hole for generating capillary force becomes saturated with sheath liquid, the flow rate for suctioning the sheath liquid is liable to become unstable. Accordingly, it is also possible to use a suction device in combination with the sheath liquid suction means so stabilize the flow rate of the sheath liquid. For example, it is possible to bring one end of a sheath liquid suction pad such as cotton into contact with the sheath liquid to absorb the sheath liquid while also suctioning the sheath liquid absorbed into the sheath liquid suction pad from the other end of the sheath liquid suction pad using a suction pump or other suction device. It is also possible to suction the sheath liquid by capillary force from one end of the hole 525 capable of suctioning the sheath liquid by capillary force while also suctioning the sheath liquid using a suction device from the suction port in communication with the hole 525. It is furthermore possible to omit the hole 525 from the advection-aggregation unit 52, and to insert a suction pad into the suction port and bring the suction port into contact with the planar section 41 so as to adjust the magnitude of the capillary force generated in the suction port connected to the sheath-liquid-suctioning pump or other suctioning device.

Figure 17:
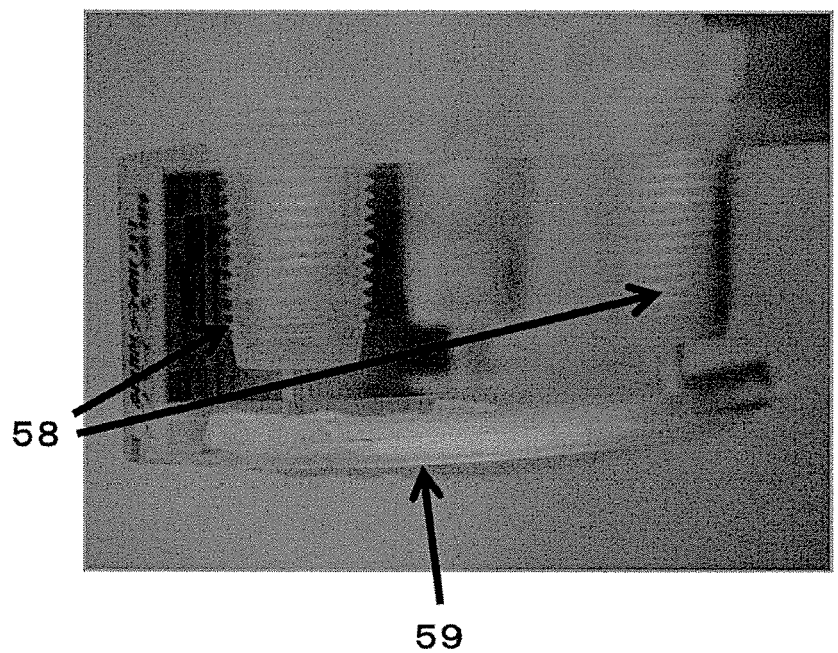
FIG. 17 is a photograph in place of a drawing showing an enlarged side view of the advection-aggregation unit.

FIG. 17 is a photograph from the side surface of the advection-aggregation unit 52 and is a photograph showing a sheath liquid suction pad 59 mounted in the hole 525 and a tube 58 made of silicone or the like connected to the sheath liquid suction port 526.

The material constituting the advection-aggregation unit is not particularly limited and may be acrylic, nylon, Teflon (registered trademark), or other resin, or glass or the like, as long as it does not react with the sample liquid or the sheath liquid. The advection-aggregation unit 52 can be fabricated by cutting using a drill, end mill, or other cutting tool, or by fabricating a mold in the shape of the advection-aggregation unit 52 and using injection molding. The advection-aggregation unit 52 in the present invention may be a single member or may be a combination of separately fabricated members as long as the unit includes a sheath liquid injection port 521, sample injection port 522, sheath liquid planar section 523, sample planar section 524, and furthermore, a hole 55 and sheath liquid injection port 56 formed as required.

The microparticle extraction means 53 is not particularly limited as long as the microparticles captured in the capture site 4 can be extracted, and an example includes a manipulator provided with cell-suctioning means. The microparticle extraction means 53 may be capable of automatically recovering the to-be-captured microparticles 5 captured in the capture site 4 using a manipulator in coordination with detection means for detecting the to-be-captured microparticles. For example, it is possible to use a cell-picking system such as that disclosed in JP 2010-29178 A. The method for detecting captured CTCs may be performed by fluorescent staining using anti-EpCam antibodies or other CTC-specific antibodies marked by FITC or PE, and observation by a fluorescence microscope or the like. When bright-field observation is carried out using an optical microscope, CTCs can be detected using the nucleus, cytoplasm, and other morphological feature in the cell as an indicator with the aid of a Papanicolaou stain or Giemsa stain.

When the microparticles extracted using the microparticle extraction means 53 are a biological material containing nucleic acids and PCR is to be carried out after extraction, the extracted biological material can be transferred to the PCR means 54. The PCR means can be a well-known device.

The positions of the sheath liquid planar section 523 and the sample planar section 524 are different in the radial direction, and the relative speed of the two sections is different when the chip 40 is rotated, but the chip 40 is preferably rotated so that the relative speed with the chip 40 is in a range of 50 to 1500 μm/s, more preferably 60 to 1000 μm/s. When the relative speed is less than 50 μm/s, processing time is increased and processing capacity is reduced. When the relative speed is greater than 1500 μm/s, the to-be-captured microparticles 5 are not captured and separation efficiency is reduced. In the system shown in FIG. 14, the advection-aggregation unit 52 is fixed and the chip 40 is rotated, but the chip 40 may be fixed and the advection-aggregation unit 52 may be rotated.

The amount of sample liquid to be injected varies in accordance with the height of the pillars 3 and the gap between the pillars, but the flow rate is preferably 1.0 to 10.0 μL/s per 0.72 mm$^2$ cross-sectional area of the chip 40 when, e.g., when the chip is formed in a substantially hexagonal planar packed state in which the height of the pillars 3 is 30 μm and the gap between the pillars 3 is 6 μm. When the amount is less than 1.0 μL, processing time is increased and processing capacity is reduced. When the amount is greater than 10 μL, the sample cannot be held between the chip and the sample planar section of the advection-aggregation unit, which is not desirable. The sheath liquid can be injected so as to be the same as the amount of sheath liquid to be suctioned. The amount sample liquid and/or sheath liquid per cross-sectional area is the same in other embodiments.

The microparticle separation system of the present invention may be provided with a magnetic field generator and/or an electric field generator for increasing the efficiency of capturing to-be-captured microparticles in the capture sites. For example, it is possible form a disc portion using a permanent magnet or the like on the rotation means 51 to correspond to the portion in which the capture site 4 is formed, and to install a permanent magnet or an electromagnet as a magnetic field generator on the lower surface of the disc portion to generate a potential field of a magnetic field, and impart magnetism to the CTCs to which magnetic particles marking EpCAM antibodies or the like have been specifically adsorbed, or CTCs to which magnetic particles have been nonspecifically adsorbed (taken in from endocytosis), or other to-be-captured particles, and when the microparticle separation system of the present invention is used, separation of objective particles from other particles not marked with magnetism can be carried out with good precision.

It is also possible to provide an electrode as an electric field generator on the disc portion corresponding to the capture sites or the lower side of the disc portion to generate a potential field of an electric field (in a non-uniform electric field), and to assist capture of CTCs using the polarization of the CTCs and peripheral media and the electrostatic force (Coulomb's force) generated by the slope of the electric field. When the chip is not rotated, a magnetic field generator and/or an electric field generator or the like can be provided below the capture site 4.

The microparticle extraction means 53, PCR means 54, detection means, and the like shown in FIG. 14 may be used in the microparticle separation system shown in FIGS. 8 and 10. When the microparticle extraction means 53, PCR means 54, and detection means in the embodiment shown in FIG. 10 are to be used, the microparticle extraction means 53 can be used after advection and aggregation has completed and after the cover plate 31 has been removed.

Figure 18:
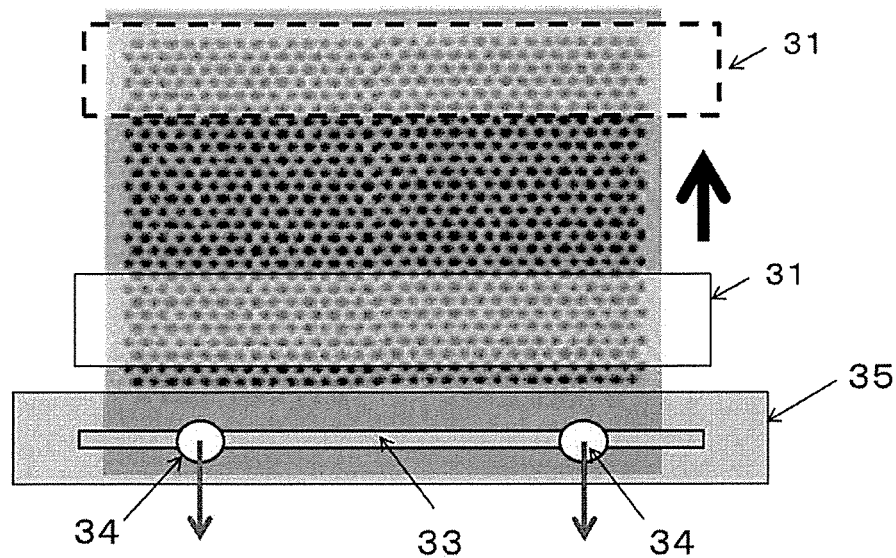
FIG. 18 shows another embodiment of the microparticle separation system of the present invention.

FIG. 18 shows another embodiment of the microparticle separation system. As described above, when microparticle extraction means 53, PCR means 54, and detection means are to be used in the microparticle separation system shown in FIG. 10, the cover plate 31 must be removed after completion of advection and aggregation. Consequently, the to-be-captured microparticles 5 cannot be recovered until after all the sample liquid has flowed, and, for example, when cancer cells or other living cells are to be captured, the cells are liable to die. In the embodiment shown in FIG. 18, the cover plate 31 has a size that covers a portion of the capture site 4, and a meniscus is generated by moving the cover plate 31 or the chip 1. Moving the cover plate 31 or the chip 1 allows the area above the to-be-captured microparticles 5 captured by the meniscus in the capture site 4 to be in an immediately open state, and the to-be-captured microparticles 5 can therefore be sampled rapidly by the microparticle extraction means 53. The movement speed of the cover plate 31 can be the same as the movement speed of the thin plate 21 for a sample shown in FIG. 8. It is also possible to provide a hole (not shown) to the cover plate 31 and continuously feed the sample liquid and the sheath liquid.

The present invention is described in detail below using examples, but the examples are used merely for describing the present invention and are provided as reference for concrete modes thereof. Although these examples described specific concrete modes of the present invention, the examples do not limit the scope of the invention disclosed in the present application and do not represent any limitation.

EXAMPLES

Example 1

[Chip Fabrication]

First, a silicon substrate was organically washed with acetone, ethanol, and ultrapure water, in the stated sequence, using an ultrasonic washer for 5 minutes each at 45 kHz, and then baked for 20 minutes at 145° C. Next, SU-8 was spin-coated onto the silicon substrate and then prebaked for 30 minutes at 95° C. on a hot plate. Exposure was subsequently carried out using a chrome mask in which equilateral hexagons were disposed adjacent to each other to obtain a planar packed state, after which post-exposure baking was carried out for two minutes at 95° C. on a hot plate, and development was performed using a PM thinner. After development, rinsing was carried out using ethanol and ultrapure water, and the moisture was dispersed and drying was carried out using a spin dryer or the like to fabricate a template. The fabricated template was transferred to polydimethylsiloxane (PDMS); and after transfer, the two were separated from each other, and the PDMS to which the template had been transferred was affixed to a glass plate. The PDMS surface was therefore hydrophilized using a plasma treatment (frequency 50 kHz and output 700 W for 30 seconds) to fabricate a chip.

Figure 19:
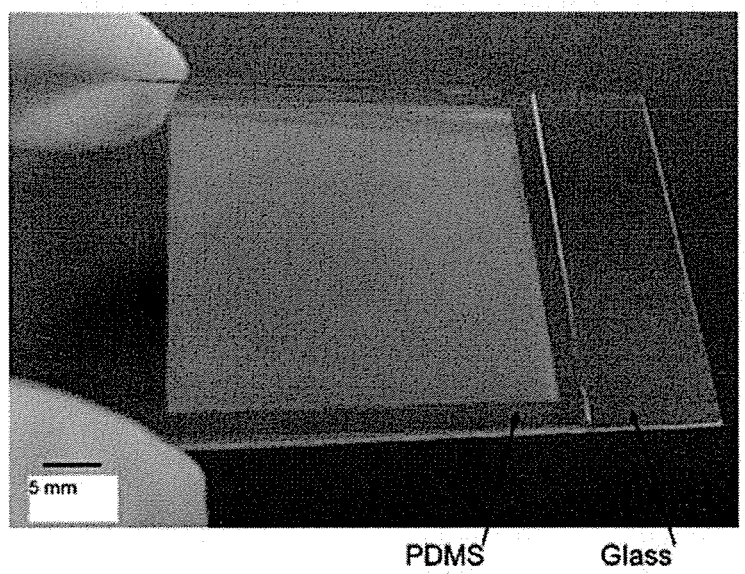
FIG. 19 is a photograph in place of a drawing showing the external appearance of the chip for fabricated in Example 1.

FIG. 19 is a photograph showing the external appearance of the chip for fabricated in Example 1, the size of the chip being 50 mm×30 mm. The size of the formed capture sites was 26 mm×24 mm.

Figure 20:
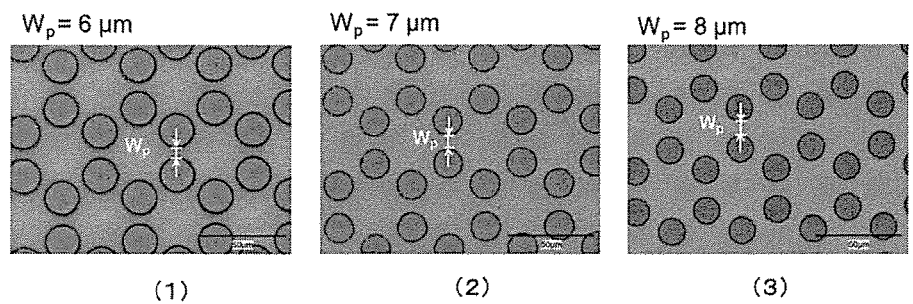
FIG. 20 is a photograph in place of a drawing showing an enlarged view of the capture sites of the chips fabricated in examples 1 to 3.

FIG. 20(1) is an enlarged photograph the capture sites, the diameter of the pillars being about 20 μm, the spacing between pillars being about 6 μm, the height of the pillars being about 30 μm, and the size of the capture sites being about 30 μm.

Example 2

In place of the chrome mask of Example 1, a chrome mask was fabricated using the same procedure as in Example 1, except that a chrome mask having a spacing of about 7 μm between pillars was used. FIG. 20(2) is an enlarged photograph the capture sites fabricated in Example 2.

Example 3

In place of the chrome mask of Example 1, a chrome mask was fabricated using the same procedure as in Example 1, except that a chrome mask having a spacing of about 8 μm between pillars was used. FIG. 20(3) is an enlarged photograph the capture sites fabricated in Example 3.

Example 4

[Fabrication of a Blood Sample]

Cells ($1.1 \times 10^4$) of a stomach cancer cell strain (human stomach cancer-derived cell strain (GCIY-GFP) dispersed by trypsinization) were suspended in 40 μL of drawn human blood to which 160 μL of phosphate-buffered saline (PBS) had been added to fabricate a blood sample that simulates cancer patient blood. The average particle diameter of the cancer cells was 25 μm.

[Fabrication of a Microparticle Separation System and Experiment for Separating CTCs from a Blood Sample]

Figure 21:
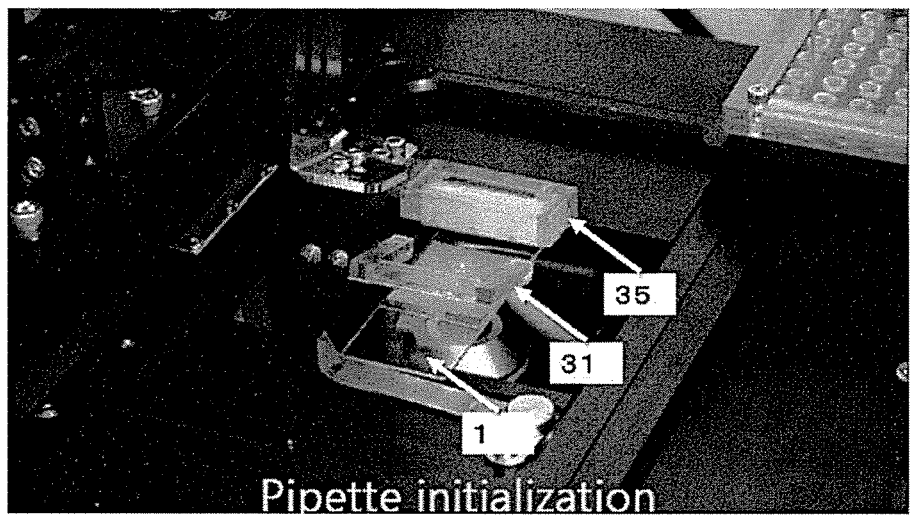
FIG. 21 shows the microparticle separation system used in the experiment for separating CTC from a blood sample.
Figure 22:
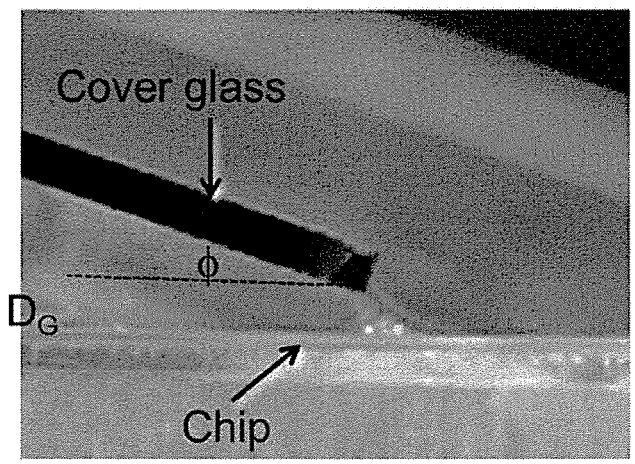
FIG. 22 is a photograph in place of a drawing showing a side view of the arrangement relationship of the chip and cover plate.

FIG. 21 shows the microparticle separation system used in the experiment for separating CTC from a blood sample. A cover plate 31 (25 mm×35 mm) made of glass and a suction unit 35 (plastic, external shape: width 38 mm, length 18 mm, height 7 mm; insertion portion: width 30 mm, length 10 mm, depth 5 mm) into which dental cotton (diameter: 10 mm; length: mm) had been inserted were disposed on the chip 1 fabricated in Example 1. FIG. 22 is a photograph showing a side view of the arrangement relationship of the chip 1 and cover plate 31. The micro-stage was adjusted so that the spacing $D_G$ between the chip 1 and the tip of the cover plate 31 was 500 μm and the angle φ between the chip 1 and the cover plate 31 was 10 degrees. Next, 200 μL of the blood sample was injected into the tip portion of the cover plate 31 and the chip 1. The chip 1 was subsequently moved at a constant speed of 40 μm/s in the upward direction of FIG. 21. The movement speed was a speed that allowed the 200-μL sample to separate in 1.5 minutes. The number of GCIY-GFP cells was counted before the sample was allowed to flow, and the GCIY-GFP cells captured in the capture sites were counted after separation to thereby measure the capture rate.

Example 5

The capture rate was measured using the same procedure as in Example 4, except that the chip fabricated in Example 2 was used in lieu of the chip fabricated in Example 1.

Example 6

The capture rate was measured using the same procedure as in Example 4, except that the chip fabricated in Example 3 was used in lieu of the chip fabricated in Example 1.

Table 1 shows the capture rate for Examples 4 to 6. It is apparent from Table 1 that the spacing between pillars is preferably narrowed in the case of cells or the like in which the to-be-captured microparticles 5 readily change shape.

TABLE 1

|  | Pillar spacing | Cell count in sample | Number of captured cells | Capture rate (%) |
|---|---|---|---|---|
| Example 4 | 6 μm | 19 | 18 | 95 |
| Example 5 | 7 μm | 8 | 8 | 100 |
| Example 6 | 8 μm | 24 | 15 | 63 |

Example 7

The capture rate was measured using the same procedure as in Example 4, except that the movement speed of the cover plate was set to a speed that allowed a 200-μL sample to separate in 7 minutes.

Example 8

The capture rate was measured using the same procedure as in Example 4, except that the movement speed of the cover plate was set to a speed that allowed a 200-μL sample to separate in 3.5 minutes.

Example 9

The capture rate was measured using the same procedure as in Example 4, except that the movement speed of the cover plate was set to a speed that allowed a 200-μL sample to separate in 1 minute.

Figure 23:
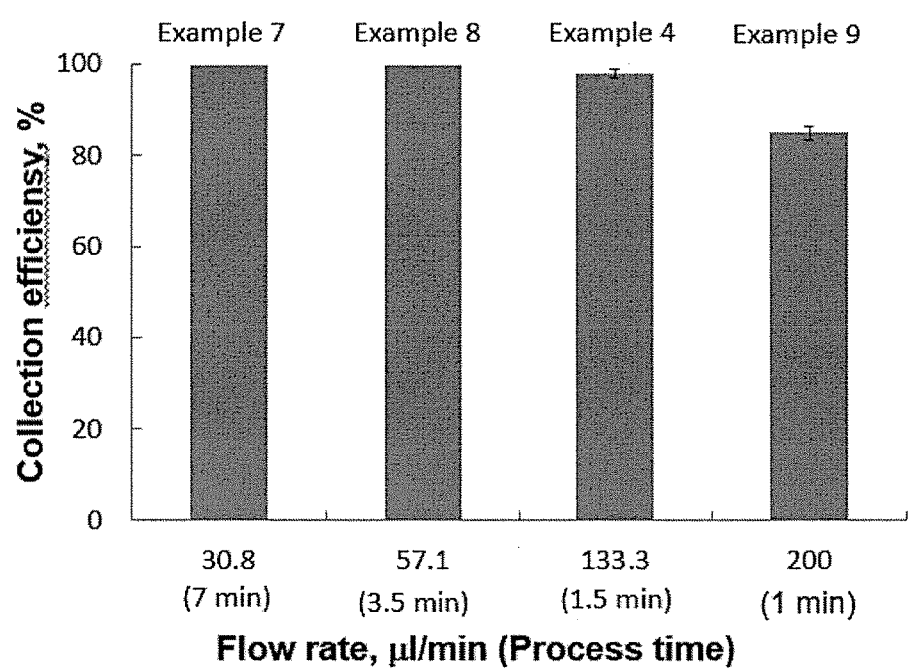
FIG. 23 is a graph showing the capture rate for example 4, and examples 7 to 9.
Figure 24:
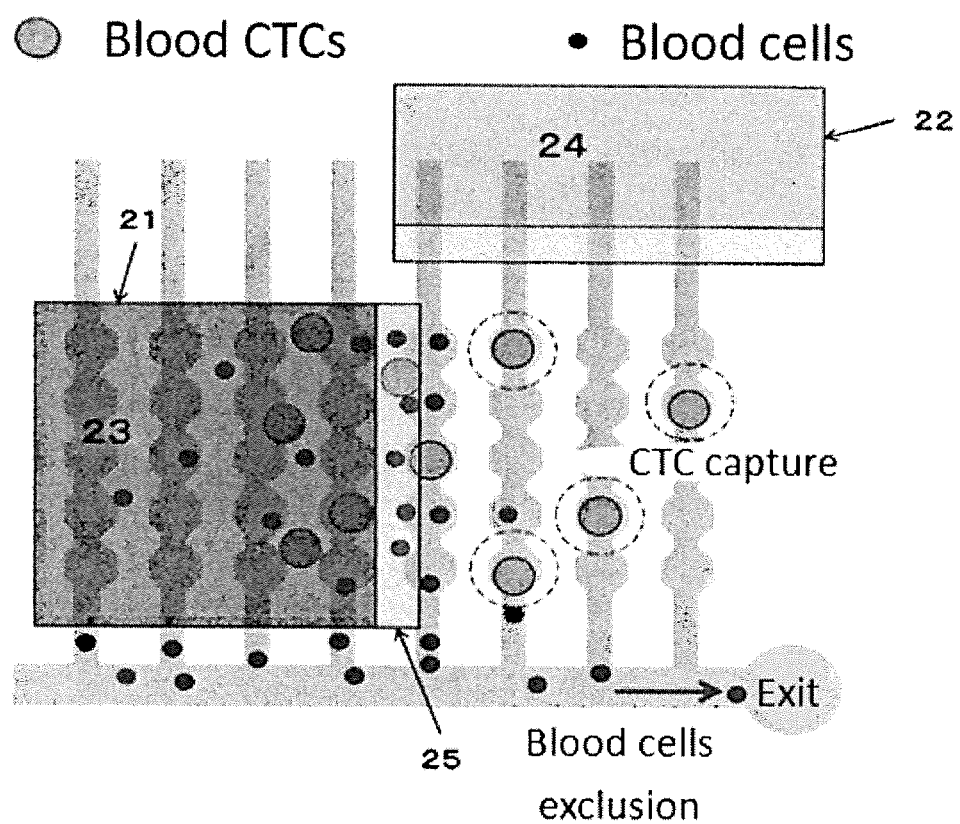
FIG. 24 shows the microparticle separation system using a related microchannel microparticle separation chip.

FIG. 23 is a graph showing the capture rate for example 4, and examples 7 to 9. It is apparent from FIG. 23 that a GCIY-GFP cell count in excess of 80% was captured even when the chip 1 was moved at a speed that allowed a 200-μL sample to separate in 1 minute. In the case of a microparticle separation system using a related microchannel microparticle separation chip (fabricated using Example 1 of Japanese Patent Application No. 2012-227717, length 30 mm, width 30 mm; substantially octagonal capture sites: diagonal length 30 μm, depth about 30 μm; microchannels: width about 10 μm, channel depth in capture sites about 20 μm, channel depth in non-capture sites about 50 μm, and center distance between channels about 60 μm) as shown in FIG. 24, the practical sample separation capacity was 10 μL/min. Therefore, the throughput can be improved by about 20 times by using the chip of the present invention in comparison with a related microchannel microparticle separation chip.

INDUSTRIAL APPLICABILITY

Using the microparticle separation system comprising the chip of the present invention makes it possible to rapidly separate out microparticles of different sizes in a sample with high efficiency without the use of antibodies or the like. Separation of CTCs from whole blood and other applications are therefore very effective in a clinical setting, and the system can therefore be used as a system for cancer diagnosis in hospitals, emergency centers, and other medical institutions, as well as in university medical departments and other research institutions and educational institutions.

The invention claimed is:

1. A microparticle separation system comprising:
a microparticle separation chip;
a first thin plate for a sample liquid;
a second thin plate for a sheath liquid; and at least one selected from the group consisting of a suction material and a suction device, for suctioning the sheath liquid, wherein:

the microparticle separation chip comprises a substrate and at least three or more pillars, each having one end provided on the substrate and the other end being open above, a single capture site for capturing to-be-captured microparticles is formed by the at least three or more pillars, a spacing Z between any mutually adjacent pillars that form the single capture site satisfies Y<Z≤X, where X is a size of the to-be-captured microparticles, and Y is a size of the microparticles to be removed, the at least three or more pillars that form the single capture site are arranged in a positional relationship in which to-be-captured microparticles captured in the capture site do not flow out from between any adjacent pillars, the first thin plate and the second thin plate are provided so that a gap of 200 μm to 1000 μm is formed between the first and second thin plates and a pillar-opening side of the microparticle separation chip, and the at least one selected from the group consisting of a suction material and a suction device is arranged on an external periphery of the microparticle separation chip.

2. The microparticle separation system according to claim 1, wherein: a single cover plate is provided as the first thin plate and the second thin plate;

the single cover plate is provided so that the gap of 200 μm to 1000 μm is formed between the single cover plate and the pillar opening side of the microparticle separation chip.

3. The microparticle separation system according to claim 1, wherein the spacing Z between the any mutually adjacent pillars satisfies one relationship selected from the group consisting of 0.8Y<Z≤0.8X, Y<Z≤0.8X, and 0.8Y<Z≤X.

4. The microparticle separation system according to claim 2, wherein the spacing Z between the any mutually adjacent pillars satisfies one relationship selected from the group consisting of 0.8Y<Z≤0.8X, Y<Z≤0.8X, and 0.8Y<Z≤X.

5. The microparticle separation system according to claim 1, wherein a plurality of capture sites is formed.

6. The microparticle separation system according to claim 2, wherein a plurality of capture sites is formed.

7. The microparticle separation system according to claim 1, wherein the substrate is polygonal or circular and a stepped part is formed at an external periphery of the substrate.

8. The microparticle separation system according to claim 2, wherein the substrate is polygonal or circular and a stepped part is formed at an external periphery of the substrate.

9. The microparticle separation system according to claim 1, wherein the substrate is polygonal and a planar section in which no pillar is formed is formed at an external periphery of the substrate.

10. The microparticle separation system according to claim 2, wherein the substrate is polygonal and a planar section in which no pillar is formed is formed at an external periphery of the substrate.

11. The microparticle separation system according to claim 1, wherein the substrate is circular and a planar section in which no pillar is formed is formed at an external periphery of the substrate.

12. The microparticle separation system according to claim 2, wherein the substrate is circular and a planar section in which no pillar is formed is formed at the external periphery of the substrate.

13. The microparticle separation system according to claim 1, furthermore comprising a suction unit having a lateral groove formed on one surface side of a base member and a suction hole that is in communication with the lateral groove and that passes through the base member to an opposite surface side of the one surface side of the base member, the suctioning unit being arranged on the external periphery of the microparticle separation chip.

14. The microparticle separation system according to claim 2, furthermore comprising a suction unit having a lateral groove formed on one surface side of a base member and a suction hole that is in communication with the lateral groove and that passes through the base member to an opposite surface side of the one surface side of the base member, the suctioning unit being arranged on the external periphery of the microparticle separation chip.

15. The microparticle separation system according to claim 1, wherein:

the substrate of the microparticle separation chip is circular and a planar section in which no pillar is formed is formed at an external periphery of the substrate, and the microparticle separation system comprises, as the first thin plate and the second thin plate, an advection-aggregation unit including a sheath liquid injection port, a sample injection port, a planar section for sheath liquid advection and aggregation, and a planar section for sample advection and aggregation.

16. The microparticle separation system according to claim 15, wherein the advection-aggregation unit further comprises a sheath liquid suction port and a hole for mounting a sheath liquid suction pad.

17. The microparticle separation system according to claim 15, wherein the advection-aggregation unit further comprises a sheath liquid suction port and a hole for suctioning the sheath liquid by capillary force.

18. A microparticle separation method in which a microparticle separation chip is used, the microparticle separation chip comprising:
a substrate and at least three or more pillars, each having one end provided on the substrate and the other end being open upward;

a single capture site for capturing to-be-captured microparticles, the single capture site being formed by the at least three or more pillars, a spacing Z between any mutually adjacent pillars that form the single capture site satisfying Y<Z≤X, where X is a size of the to-be-captured microparticles, and Y is a size of the microparticles to be removed, the at least three or more pillars that form the single capture site being arranged in a positional relationship in which to-be-captured microparticles captured in the capture site do not flow out from between any adjacent pillars, the microparticle separation method comprising:
placing a first thin plate for the sample liquid and a second plate for the sheath liquid over a pillar-open side of the microparticle separation chip so that a gap of 200 μm to 1000 μm is formed between the first and second thin plates and the pillar-opening side of the microparticle separation chip;

injecting a sample liquid in between the first thin plate and the microparticle separation chip;

injecting a sheath liquid in between the second thin plate and the microparticle separation chip;

suctioning the sheath liquid; and by causing the microparticle separation chip, the first thin plate, and the second thin plate to move in a relative fashion to generate a meniscus, capturing to-be-captured microparticles in capture sites provided to the microparticle separation chip from the pillar-open side, and removing microparticles to be removed from the microparticle separation chip by the sheath liquid suctioned.

19. The microparticle separation method according to claim 18, wherein a single cover plate is used as the first thin plate and the second thin plate.

20. The microparticle separation method according to claim 19, the method further comprising: washing away remaining microparticles to be removed by the sheath liquid suctioned.

21. The microparticle separation method according to claim 18, wherein:

the substrate of the microparticle separation chip is circular and a planar section in which no pillar is formed is formed at an external periphery of the substrate, as the first thin plate and the second thin plate, an advection-aggregation unit is used, the advection-aggregation unit includes a sheath liquid injection port, a sample injection port, a planar section for sheath liquid advection and aggregation, and a planar section for sample advection and aggregation, and the microparticle separation method comprises:

mounting the microparticle separation chip on a rotator for rotating the microparticle separation chip;

arranging the advection-aggregation unit on a surface of the microparticle separation chip;

injecting the sheath liquid from the sheath liquid injection port and injecting the sample liquid from the sample injection port while the rotator is rotated to thereby move the microparticle separation chip and the planar section for sheath liquid advection and aggregation and the planar section for sample advection and aggregation in a relative fashion, and capture objective microparticles in the capture sites formed in the microparticle separation chip, with aid of a meniscus generated by the relative movement; and removing the microparticles to be removed, together with the sheath liquid from the microparticle separation chip, by suctioning the sheath liquid.

* * * * *